(12) United States Patent
Fujiwara et al.

(10) Patent No.: US 8,389,746 B2
(45) Date of Patent: Mar. 5, 2013

(54) CYCLIC CARBONYL COMPOUNDS WITH PENDANT CARBONATE GROUPS, PREPARATIONS THEREOF, AND POLYMERS THEREFROM

(75) Inventors: Masaki Fujiwara, Tokyo (JP); James Lupton Hedrick, Pleasanton, CA (US); Daniel Paul Sanders, San Jose, CA (US); Manabu Yasumoto, San Jose, CA (US)

(73) Assignees: International Business Machines Corporation, Armonk, NY (US); Central Glass Co., Ltd., Ube-shi, Yamaguchi (JP)

( * ) Notice: Subject to any disclaimer, the term of this patent is extended or adjusted under 35 U.S.C. 154(b) by 0 days.

(21) Appl. No.: 13/491,847

(22) Filed: Jun. 8, 2012

(65) Prior Publication Data

US 2012/0245304 A1    Sep. 27, 2012

Related U.S. Application Data

(62) Division of application No. 12/770,877, filed on Apr. 30, 2010, now Pat. No. 8,207,351.

(51) Int. Cl.
*C07D 321/00*    (2006.01)
(52) U.S. Cl. ......... 549/228; 549/229; 525/461; 528/370
(58) Field of Classification Search .................. 549/228, 549/229; 528/370; 525/461
See application file for complete search history.

(56) References Cited

U.S. PATENT DOCUMENTS

| | | | |
|---|---|---|---|
| 3,663,569 A | 5/1972 | Lew |
| 4,102,912 A | 7/1978 | Carr |
| 4,501,905 A | 2/1985 | Krimm et al. |
| 5,091,543 A | 2/1992 | Grey |
| 5,212,321 A | 5/1993 | Muller et al. |
| 5,424,473 A | 6/1995 | Galvan et al. |
| 5,466,811 A | 11/1995 | Alexander |
| 5,861,107 A | 1/1999 | Buysch et al. |
| 6,020,499 A | 2/2000 | Drysdale et al. |
| 6,054,596 A | 4/2000 | Ohno et al. |
| 6,258,962 B1 | 7/2001 | Buchanan et al. |
| 6,300,458 B1 | 10/2001 | Vandenberg |
| 6,664,372 B1 | 12/2003 | Janda et al. |
| 2007/0015932 A1 | 1/2007 | Fujita et al. |
| 2007/0232751 A1 | 10/2007 | Ludewig et al. |
| 2010/0280242 A1 | 11/2010 | Hedrick et al. |
| 2010/0305281 A1 | 12/2010 | Fujiwara et al. |
| 2010/0305300 A1 | 12/2010 | Coulembier et al. |
| 2010/0311917 A1 | 12/2010 | Hedrick et al. |
| 2010/0317838 A1 | 12/2010 | Dubois et al. |
| 2011/0150977 A1 | 6/2011 | Hedrick et al. |
| 2011/0151566 A1 | 6/2011 | Hedrick et al. |
| 2011/0152167 A1 | 6/2011 | Hedrick et al. |
| 2011/0182996 A1 | 7/2011 | Fukushima et al. |
| 2011/0243848 A1 | 10/2011 | Appel et al. |
| 2011/0269917 A1 | 11/2011 | Fujiwara et al. |

FOREIGN PATENT DOCUMENTS

WO     2005110013 A2    11/2005

OTHER PUBLICATIONS

Efimov, et al., "Dipentafluorophenyl carbonate—a reagent forthe synthesis of oligonucleotides and their conjugates," Nucleic Acids Res. 1993, 21, 5337.
European Patent Office, PCT/EP2011/056778, filing date Apr. 28, 2011, International Search Report and Written Opinion, mailing date Jun. 21, 2011.
Fujita, et al., "Phosgene-Free Synthesis of N-Carboxyanhydrides of alpha-Amino Acids Based on Bisarylcarbonates as Starting Compounds," J. Polym. Sci. A. Polym. Chem. 2007, 45, 5365-5369.
Han, et al., "Azatides: Solution and Liquid Phase Syntheses of a New Peptidomimetic," JACS, 1996, 2539-2544.
Han, et al., "Investigations of Azapeptides as Mimetics of Leu-Enkephalin," Bioorg. Med. Chem. 1998, 8, 117-120.
Kuling, et al., "Synthesis of poly(2-ethyl-2-hydroxymethyltrimethylene carbonate)," MakromolChem, v192, p. 1193-1205 (1991); first published online: Mar. 12, 2003.
Pratt, Russell C., et al.,"Tagging alcohols with cyclic carbonate: a versatile equivalent of (meth)acrylate for ring-opening polymerization", Chem. Commun., 2008, pp. 114-116, Dec. 25, 2007.
Simon, et al., "Abstracts of the CPIMA Technical Forum, 2009" Retrieved from the Internet: RL:http://cpima.stanford.edu/forum2009/?s orted_by=abstracts [retrieved on Jun. 1, 2011] Abstract No. 5.
USPTO, Non-final Office Action, U.S. Appl. No. 12/770,877, Nov. 23, 2011.
Xie, et al., "Synthesis and characterization of novel biodegradable poly(carbonate ester)s with photolabile protecting groups", Biomacromolecules, vol. 9(1), pp. 376-380, published on web Dec. 8, 2007.

*Primary Examiner* — Shane Fang
(74) *Attorney, Agent, or Firm* — Michael R. Roberts

(57) ABSTRACT

A one pot method of preparing cyclic carbonyl compounds comprising an active pendant pentafluorophenyl carbonate group is disclosed. The cyclic carbonyl compounds can be polymerized by ring opening methods to form ROP polymers comprising repeat units comprising a side chain pentafluorophenyl carbonate group. Using a suitable nucleophile, the pendant pentafluorophenyl carbonate group can be selectively transformed into a variety of other functional groups before or after the ring opening polymerization.

20 Claims, No Drawings

CYCLIC CARBONYL COMPOUNDS WITH PENDANT CARBONATE GROUPS, PREPARATIONS THEREOF, AND POLYMERS THEREFROM

CROSS REFERENCE TO RELATED APPLICATIONS

This application is a division of, and claims the benefit of, pending nonprovisional U.S. application Ser. No. 12/770,877 entitled "CYCLIC CARBONYL COMPOUNDS WITH PENDANT CARBONATE GROUPS, PREPARATIONS THEREOF, AND POLYMERS THEREFROM" filed on Apr. 30, 2010, herein incorporated by reference in its entirety.

PARTIES TO A JOINT RESEARCH AGREEMENT

International Business Machines Corporation, a New York corporation, and Central Glass Co., Ltd., a Ube-shi, Yamaguchi, Japan corporation, are parties to a Joint Research Agreement.

BACKGROUND

The present disclosure is generally related to cyclic carbonyl compounds for ring-opening polymerizations and methods of preparation thereof, and more specifically to cyclic carbonate compounds having a pendant pentafluorophenyl carbonate group. In addition, the disclosure also relates to the preparation of polymers having pendant pentafluorophenyl carbonate groups, which can be further reacted to form functionalized polymeric materials.

In general, the structural variety of cyclic carbonyl compounds for ring opening polymerization (ROP) is significantly less than the number of compounds available for controlled radical polymerization (CRP). However, as the effectiveness and operational simplicity of organocatalysts improves, a wider variety of ROP compounds is sought to generate polymer microstructures unique to ROP methods.

Initial efforts to employ substituted lactones as monomers for ROP were hampered by the sensitivity of the organocatalysts to steric bulk of the substituent groups, particularly those at the alpha-position. Since the alpha-position of cyclic esters is the only site capable of a general substitution reaction, this approach provided limited numbers of useful compounds. The finding that trimethylene carbonate (TMC) was efficiently polymerized by organocatalysts such as thiourea/1,8-diazabicyclo[5.4.0]undec-7-ene (TU/DBU) or 1,5,7-triazabicyclo[4.4.0]dec-5-ene (TBD) was encouraging, for two reasons: first, TMC-like compounds can be derived from readily available 1,3-diols, and second, the 1,3-diols can be chosen so as to only bear substituents at the 2-position, which becomes the 5-position in the cyclic carbonate, where the substituent does not interfere sterically with the ring-opening polymerization.

A number of cyclic carbonate compounds have been generated and polymerized in the past by more conventional anionic or organometallic ROP methods. Excessively bulky substituents (e.g., 2,2-diphenyl) in the 1,3-diol can make ring-opening of the corresponding cyclic carbonate thermodynamically unfavorable. Thus, efforts were focused on compounds derived from 2,2-bis(methylol)propionic acid (bisMPA), a common building block for biocompatible dendrimers. For example, cyclic carbonate compounds with a number of different functional groups attached to the carboxylate have been generated from bisMPA (Pratt et al. *Chem. Comm.* 2008, 114-116), Scheme 1.

Scheme 1.

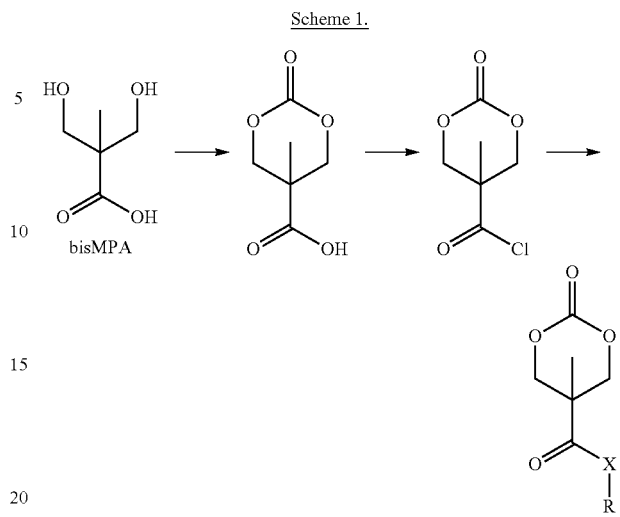

wherein X is O, NH, NR', or S, and R' and R generally represent groups comprising 1 to 30 carbons. The —COXR group can, for example, represent an ester, amide, or thioester derived from the bisMPA carboxylic acid.

The cyclic carbonate acid compound, MTCOH,

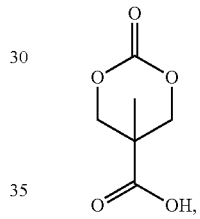

(MTCOH)

provides great versatility in preparing functionalized carbonate compounds for ROP, similar to (meth)acrylic acid for CRP. For example, the reaction of an alcohol or amine with (meth)acrylic acid (or (meth)acryloyl chloride) provides a (meth)acrylate or (meth)acrylamide compound for CRP. Likewise, the reaction of an arbitrary alcohol or amine with MTCOH (or its acid chloride) can generate a cyclic carbonate ester or cyclic carbonate amide compound for ROP.

However, there are only a few cyclic ester compounds bearing pendant carbonate or carbamate groups reported in the literature. For example, a cyclic carbonate bearing a chloroformate pendant group, MTCOCOCl, can be synthesized from tris(hydroxymethyl)ethane (TME) (Scheme 2).

Scheme 2.

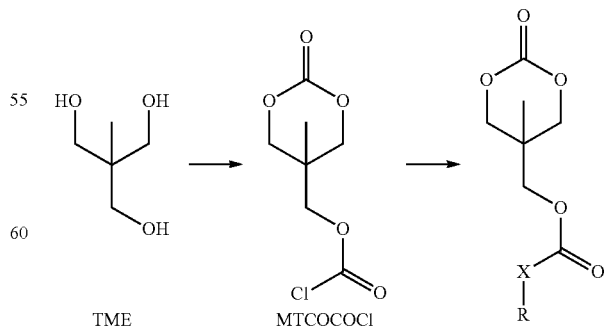

Further substitution of the acyl chloride can afford functionalized carbonate compounds; however, the chloroformate intermediate suffers from the known limitations of acid chlorides (sensitivity to water, release of corrosive hydrogen chloride gas, difficulties in shipping and storing). In addition, this synthetic route is labor and resource intensive, uses significant amounts of solvent and reagents, and is not environmentally "green."

Therefore, a need continues for improved methods of synthesis of cyclic ester compounds containing pendant carbonate or carbamate groups.

Biodegradable polymers are of intense for use in a variety of applications including drug delivery/target therapeutics, imaging agents, and tissue engineering. The two most common approaches to the synthesis of biodegradable polymers are the ring-opening polymerization (ROP) of cyclic esters (e.g., lactones) and cyclic carbonates to produce polyesters and polycarbonates, respectively, illustrated in Scheme 3.

Scheme 3.

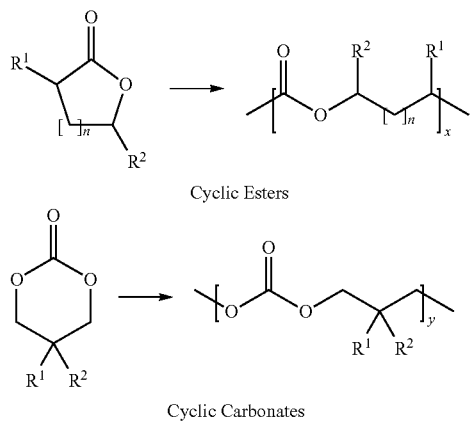

Cyclic Esters

Cyclic Carbonates wherein $R^1$ and $R^2$ generally represent hydrogen or a short chain monovalent hydrocarbon substituent, and n is 1 to 5. As a class of biodegradable polymers, polycarbonates have generally been found to exhibit significantly increased rates of biodegradation in the human body relative to polyesters.

MTCOH-based polymers have been widely reported with a variety of side chain groups. In these polymers, the side chain groups may be incorporated prior to polymerization via the synthesis of a functionalized monomer. Alternatively, cyclic carbonate monomers based on a protected variant of MTC-OH (most commonly the benzyl ester shown) can be polymerized and desired substituent groups later added to the polymer via post-polymerization modification (as shown in Scheme 4). This post-polymerization modification process typically encompasses removing the protecting group followed by coupling a new substituent group to the carboxylic acid group via the formation of an ester linkage, an amide linkage, or the like.

Scheme 4.

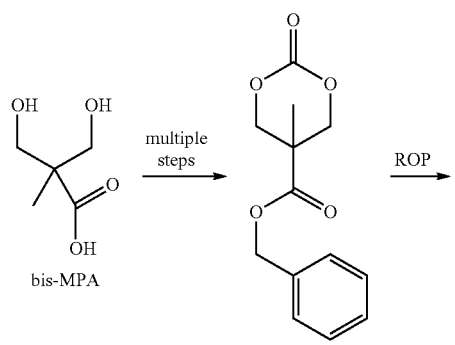

bis-MPA

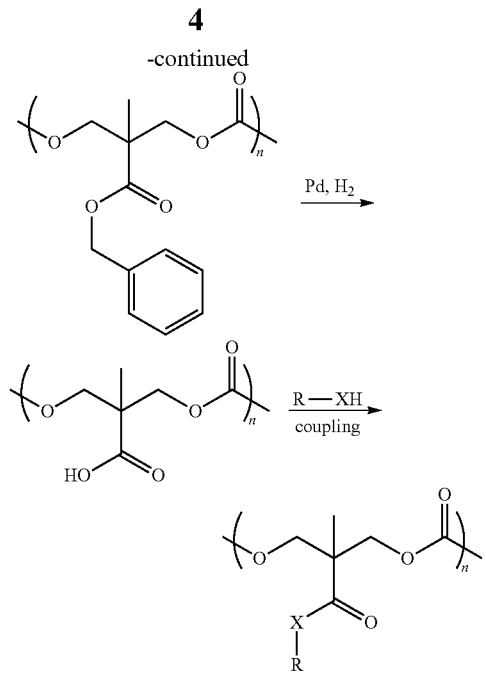

However, as a result of the limitations of the known art, few polymers bearing substituent groups attached by side-chain carbonate, carbamate, or other such linkages are known. A more versatile and straightforward approach to the preparation of ROP polymers bearing functionalized side chain groups is needed, in particular polycarbonates bearing reactive carbonate side chain groups. The reactive side chain groups should enable direct functionalization of the ROP polymer.

SUMMARY

Accordingly, disclosed is a composition, comprising:
a first cyclic carbonyl compound of the general formula (2):

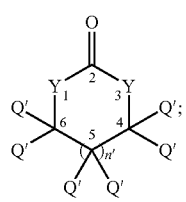

(2)

wherein
each Y is a divalent radical independently selected from the group consisting of —O—, —S—, —N(H)—, or —N(Q")-, wherein each Q" group is a monovalent radical independently selected from the group consisting of alkyl groups comprising 1 to 30 carbons, aryl groups comprising 6 to 30 carbons, and the foregoing Q" groups substituted with a pentafluorophenyl carbonate group,
n' is 0 or an integer from 1 to 10, wherein when n' is 0, carbons labeled 4 and 6 are linked together by a single bond,
each Q' group is a monovalent radical independently selected from the group consisting of hydrogen, halides, pentafluorophenyl carbonate group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing Q' groups substituted with a pentafluorophenyl carbonate group, and wherein one or more of the Q' and/or Q" groups comprises a pentafluorophenyl carbonate group.

Also disclosed is composition, comprising:

a first cyclic carbonate compound of the general formula (5):

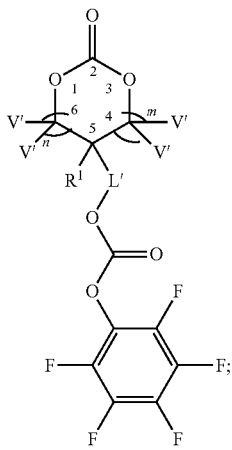

wherein m and n are each independently 0 or an integer from 1 to 11, wherein m and n cannot together be 0, and m+n is less than or equal to 11, $R^1$ is a monovalent radical selected from the group consisting of hydrogen, halides, and alkyl groups comprising 1 to 30 carbons, each V' group is monovalent radical independently selected from the group consisting of hydrogen, halides, pentafluorophenyl carbonate group (—$OCO_2C_6F_5$), alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing V' groups substituted with a pentafluorophenyl carbonate group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

A method is disclosed, comprising:

forming a first mixture comprising bis(pentafluorophenyl) carbonate, a catalyst, an optional solvent, and a precursor compound, the precursor compound comprising i) three or more carbons, ii) a first hydroxy group capable of forming a pentafluorophenyl carbonate in a reaction with bis(pentafluorophenyl) carbonate, and iii) two nucleophilic groups independently selected from the group consisting of alcohols, amines, and thiols, the two nucleophilic groups capable of forming a cyclic carbonyl group in a reaction with bis(pentafluorophenyl) carbonate;

agitating the first mixture, thereby forming a first cyclic carbonyl compound comprising i) a pendant pentafluorophenyl carbonate group and ii) a cyclic carbonyl moiety selected from the group consisting of cyclic carbonates, cyclic ureas, cyclic carbamates, cyclic thiocarbamates, cyclic thiocarbonates, and cyclic dithiocarbonates.

Another method comprises:

agitating a first mixture comprising i) a precursor compound comprising two or more carbons and three or more hydroxy groups, ii) bis(pentafluorophenyl) carbonate, and iii) a catalyst, thereby forming a first cyclic carbonate compound comprising a pendant pentafluorophenyl carbonate group.

Yet another method comprises:

forming a mixture comprising i) a first cyclic carbonyl compound comprising a cyclic carbonyl moiety selected from the group consisting of cyclic carbonates, cyclic ureas, cyclic carbamates, cyclic thiocarbamates, cyclic thiocarbonates, and cyclic dithiocarbonates, and a pendant pentafluorophenyl carbonate group, ii) a nucleophile selected from the group consisting of alcohols, amines, and thiols, iii) an optional catalyst, and iv) an optional solvent;

agitating the mixture, thereby forming a second cyclic carbonyl compound and pentafluorophenol byproduct, wherein the second cyclic carbonyl compound comprises a second functional group formed by a reaction of the pendant pentafluorophenyl carbonate group with the nucleophile, the second functional group selected from the group consisting of carbonates other than pentafluorophenyl carbonate, carbamates, and thiocarbonates.

Still another method comprises:

agitating a first mixture comprising a catalyst, an initiator, an optional accelerator, an optional solvent, and a first cyclic carbonyl compound comprising a pentafluorophenyl carbonate group, thereby forming a ROP polymer by ring opening polymerization of the first cyclic carbonyl compound, the ROP polymer comprising a chain fragment derived from the initiator, and a first polymer chain; wherein i) the chain fragment comprises a first backbone heteroatom, the first backbone heteroatom linked to a first end unit of the first polymer chain, the first backbone heteroatom selected from the group consisting of oxygen, nitrogen, and sulfur, ii) the first polymer chain comprises a second end unit comprising a nucleophilic group selected from the group consisting of hydroxy group, primary amine groups, secondary amine groups, and thiol group, and iii) the first polymer chain comprises a first repeat unit, the first repeat unit comprising a) a backbone functional group selected from the group consisting of carbonate, ureas, carbamates, thiocarbamates, thiocarbonate, and dithiocarbonate, and b) a tetrahedral backbone carbon, the tetrahedral backbone carbon being linked to a first side chain comprising a pentafluorophenyl carbonate group.

Further disclosed is a biodegradable polymer, comprising:

a chain fragment; and a first polymer chain; wherein i) the chain fragment comprises a first backbone heteroatom, the first backbone heteroatom linked to a first end unit of the first polymer chain, the first backbone heteroatom selected from the group consisting of oxygen, nitrogen, and sulfur, ii) the first polymer chain comprises a second end unit comprising a nucleophilic group selected from the group consisting of hydroxy group, primary amine groups, secondary amine groups, and thiol group, and iii) the first polymer chain comprises a first repeat unit, the first repeat unit comprising a) a backbone functional group selected from the group consisting of carbonate, ureas, carbamates, thiocarbamates, thiocarbonate, and dithiocarbonate, and b) a tetrahedral backbone carbon, the tetrahedral backbone carbon being linked to a first side chain comprising a pentafluorophenyl carbonate group.

The above-described and other features and advantages of the present invention will be appreciated and understood by those skilled in the art from the following detailed description, drawings, and appended claims.

DETAILED DESCRIPTION

Cyclic carbonyl compounds are disclosed comprising a pendant pentafluorophenyl carbonate group and a functional group selected from cyclic carbonate, cyclic carbamate, cyclic urea, cyclic thiocarbonate, cyclic thiocarbamate, cyclic dithiocarbonate, and combinations thereof. Also described is a simple one step method (Method 1) for preparing a cyclic carbonyl compound having a pendant pentafluorophenyl carbonate group, referred to herein as the first cyclic carbonyl compound. Further disclosed is a method (Method 2) of preparing a second cyclic carbonyl compound, by reacting the pendant pentafluorophenyl carbonate group of the first cyclic carbonyl compound with an alcohol, amine or thiol to form a different carbonate, a carbamate or a thiocarbonate respectively, without altering the cyclic carbonyl moiety of the first cyclic carbonyl compound. Each of the described methods is mild, high yielding, and environmentally safer than methods involving reagents such as phosgene, or intermediate acid chlorides. The first and second cyclic carbonyl compounds are potentially capable of forming biodegradable polymers by ring opening polymerization (ROP), in particular polycarbonates having unique pendant functionalities and properties.

The term "biodegradable" is defined by the American Society for Testing and Materials as a degradation caused by biological activity, especially by enzymatic action, leading to a significant change in the chemical structure of the material. For purposes herein, a material is biodegradable if it undergoes 60% biodegradation within 180 days in accordance with ASTM D6400.

The first cyclic carbonyl compound bearing a pendant pentafluorophenyl carbonate group is prepared by the reaction of bis(pentafluorophenyl) carbonate:

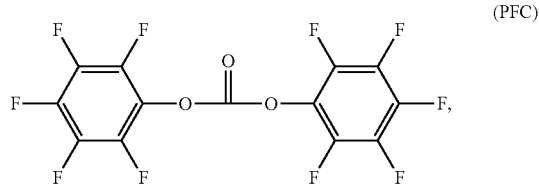 [SMILES: O=C(Oc1c(F)c(F)c(F)c(F)c1F)Oc1c(F)c(F)c(F)c(F)c1F]

(PFC)

with a precursor compound. The precursor compound comprises three or more carbons and three or more nucleophilic groups selected from the group consisting of alcohols, thiols, and amines. One of the three or more nucleophilic groups is a hydroxy group that reacts with PFC to form a pendant pentafluorophenyl carbonate group. This hydroxy group is referred to herein as a "pentafluorophenyl carbonate forming hydroxy group." Two of the three or more nucleophilic groups of the precursor compound react with PFC to form a cyclic carbonyl group, and are referred to as "cyclic carbonyl forming nucleophilic groups."

The precursor compounds have the general formula (1):

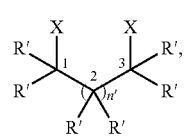

(1)

wherein together the X groups are cyclic carbonyl forming nucleophilic groups, each X independently represents a monovalent radical selected from the group consisting of —OH, —SH, —NH$_2$, and —NHR", wherein each R" group independently represents a monovalent radical selected from the group consisting of alkyl groups comprising 1 to 30 carbons, aryl groups comprising 6 to 30 carbons, and the foregoing R" groups substituted with a pentafluorophenyl carbonate forming hydroxy group, n' is 0 or an integer from 1 to 10, wherein when n' is 0 carbons labeled 1 and 3 attached to each X group are linked together by a single bond, each R' group independently represents a monovalent radical selected from the group consisting of hydrogen, pentafluorophenyl carbonate forming hydroxy group, halides, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing R' groups substituted with a pentafluorophenyl carbonate forming hydroxy group, and at least one of the foregoing R' and/or R" groups comprises a pentafluorophenyl carbonate forming hydroxy group.

The R' and R" groups can further independently comprise a cycloaliphatic ring, an aromatic ring, and/or a heteroatom such as oxygen, sulfur or nitrogen. In an embodiment, the X groups of the precursor compound are hydroxy groups capable of forming a cyclic carbonate in a reaction with PFC.

Non-limiting examples of cyclic carbonyl forming moieties include 1,2-ethanediol groups, 1,3-propanediol groups, 1,4-butanediol groups, 1,2-ethanediamine groups, 1,3-propanediamine groups, 1,4-butanediamine groups, 2-aminoethanol groups, 3-amino-1-propanol groups, 4-amino-1-butanol groups, 2-mercaptoethanol groups, 3-mercapto-1-propanol groups, 1-mercapto-2-propanol groups, 4-mercapto-1-butanol groups, cysteamine groups, 1,2-ethanedithiol groups, and 1,3-propanedithiol groups. Cyclic carbonyl groups formed by the foregoing moieties in a reaction with PFC include cyclic carbonates from any of the above diols, cyclic ureas from any of the above diamines, cyclic carbamates from any of the above amino-alcohols, cyclic thiocarbonates from any of the above mercapto-alcohols, cyclic thiocarbamates from any of the above amino-thiols, and cyclic dithiocarbonates from any of the above dithiols. These functional groups are listed in Table 1.

TABLE 1

| Cyclic Carbonyl Type | Structure |
|---|---|
| Cyclic Carbonate | O=C(O-)(O-) ring |
| Cyclic Urea | O=C(NR)(NR) ring |
| Cyclic Carbamate | O=C(NR)(O) ring |
| Cyclic Thiocarbamate | O=C(NR)(S) ring |
| Cyclic Thiocarbonate | O=C(O)(S) ring |
| Cyclic Dithiocarbonate | O=C(S)(S) ring |

The first cyclic carbonyl compound comprises a cyclic carbonyl moiety selected from the group consisting of cyclic carbonates, cyclic carbamates, cyclic ureas, cyclic thiocarbonates, cyclic thiocarbamates, cyclic dithiocarbonates, and combinations thereof, formed by reaction of the two X groups with PFC. The first cyclic carbonyl compound further comprises a pendant pentafluorophenyl carbonate group (i.e., the moiety —OCO$_2$C$_6$F$_5$) derived from a pentafluorophenyl carbonate forming hydroxy group of an R' and/or R" group.

The first cyclic carbonyl compounds are represented by the general formula (2):

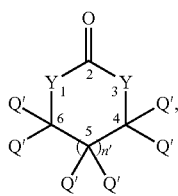

(2)

wherein
each Y is a divalent radical independently selected from the group consisting of —O—, —S—, —N(H)—, or —N(Q")-, wherein each Q" group is a monovalent radical independently selected from the group consisting of alkyl groups comprising 1 to 30 carbons, aryl groups comprising 6 to 30 carbons, and the foregoing Q" groups substituted with a pentafluorophenyl carbonate group (i.e., —OCO$_2$C$_6$F$_5$),
n' is 0 or an integer from 1 to 10, wherein when n' is 0, carbons labeled 4 and 6 are linked together by a single bond, each Q' group is a monovalent radical independently selected from the group consisting of hydrogen, halides, a pentafluorophenyl carbonate group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing Q' groups substituted with a pentafluorophenyl carbonate group, and wherein one or more of the Q' and/or Q" groups comprises a pentafluorophenyl carbonate group.

The Y groups in formula (2) are derived from the X groups of formula (1). In an embodiment, each Y in formula (2) is —O— and the first cyclic carbonyl compound comprises a cyclic carbonate group. In another embodiment, the first cyclic carbonyl compound comprises a single pendant pentafluorophenyl carbonate group.

The cyclic carbonyl group and the pendant pentafluorophenyl carbonate moiety are formed in one step from the precursor compound using PFC and a suitable catalyst. PFC is less toxic than other reagents (e.g., phosgene) in preparing cyclic carbonate compounds. PFC is a crystalline solid at room temperature that, being less sensitive to water than phosgene, can be easily stored, shipped, and handled. PFC does not require elaborate reaction and workup conditions. Moreover, the pentafluorophenol byproduct of the cyclization reaction is less volatile, less acidic, and less corrosive than hydrochloric acid. These advantages reduce the cost and complexity of the reactions, and potentially widen the scope of the starting materials to include compounds containing acid-sensitive groups. In addition, the pentafluorophenol byproduct of the cyclization reaction can be readily recycled back into PFC.

Isomerically pure precursor compounds having a hydrogen attached to an asymmetric carbon can be converted to a cyclic carbonyl compound comprising a pentafluorophenyl carbonate group without undergoing significant racemization. The esterification conditions are effective in achieving an enantiomeric excess of 80% or more, more specifically of 90%. In an embodiment, the cyclic carbonyl compound comprises an asymmetric carbon as an (R) isomer, in an enantiomeric excess of greater than 80%, more specifically greater than 90%. In another embodiment, the cyclic carbonyl compound comprises an asymmetric carbon as an (S) isomer, in an enantiomeric excess greater than 80%, more specifically greater than 90%.

More specific precursor compounds are represented by the general formula (3):

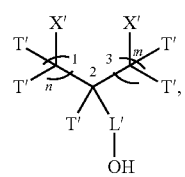

(3)

wherein
the X' groups together are cyclic carbonyl forming nucleophilic groups, m and n are each independently 0 or an integer from 1 to 11, wherein m and n cannot together be 0, and m+n is an integer less than or equal to 11, each X' is a monovalent radical independently selected from the group consisting of —OH, —SH, —NH$_2$, and —NHT", wherein each T" is a monovalent radical independently selected from the group consisting of alkyl groups comprising 1 to 30 carbons, aryl groups comprising 6 to 30 carbons, and the foregoing T" groups substituted with a pentafluorophenyl carbonate forming hydroxy group, each T' is a monovalent radical independently selected from the group consisting of hydrogen, halides, pentafluorophenyl carbonate forming hydroxy group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing T' groups substituted with a pentafluorophenyl carbonate forming hydroxy group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

The T' and T" groups can further independently comprise a cycloaliphatic ring, an aromatic ring, and/or a heteroatom such as oxygen, sulfur or nitrogen. In an embodiment, none of the T' or T" groups comprises a pentafluorophenyl carbonate forming hydroxy group. In another embodiment, the T' group attached to carbon labeled 2 in formula (3) is ethyl or methyl, and all other T' groups are hydrogen. In another embodiment, the T' group attached to carbon labeled 2 in formula (3) is ethyl or methyl, carbon labeled 2 in formula (3) is an asymmetric center, and the precursor compound comprises the (R) or (S) isomer in greater than 80% enantiomeric excess.

The corresponding first cyclic carbonyl compounds formed by the precursor compounds of formula (3) have the general formula (4):

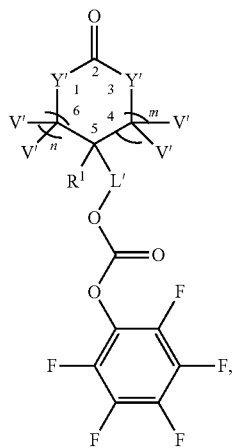

(4)

wherein
m and n are each independently 0 or an integer from 1 to 11, wherein m and n cannot together be 0, and m+n is an integer less than or equal to 11, each Y' is a divalent radical independently selected from the group consisting of —O—, —S—, —N(H)— and —N(V")—, wherein each V" group is a monovalent radical independently selected from the group consisting of alkyl groups comprising 1 to 30 carbons, aryl groups comprising 1 to 30 carbons, and a foregoing V" group substituted with a pentafluorophenyl carbonate group (—OCO$_2$C$_6$F$_5$), each V' group is a monovalent radical independently selected from the group consisting of hydrogen, halides, pentafluorophenyl carbonate group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and a foregoing V' group substituted with a pentafluorophenyl carbonate group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

In an embodiment, no V' group and no V" group comprises a pentafluorophenyl carbonate group. In another embodiment, the V' group attached to the carbon labeled 5 in formula (4) is ethyl or methyl, and all other V' groups are hydrogen. In an embodiment, the V' group attached to carbon labeled 5 in formula (4) is ethyl or methyl, carbon labeled 5 in formula (4) is an asymmetric center, and the cyclic carbonyl compound comprises the (R) or (S) isomer in greater than 80% enantiomeric excess. In another embodiment, each Y' is —O—, and V' at position labeled 5 in formula (4) is a monovalent radical selected from the group consisting of hydrogen, halides, and alkyl groups comprising 1 to 30 carbons.

Even more specific first cyclic carbonyl compounds are cyclic carbonates having the general formula (5):

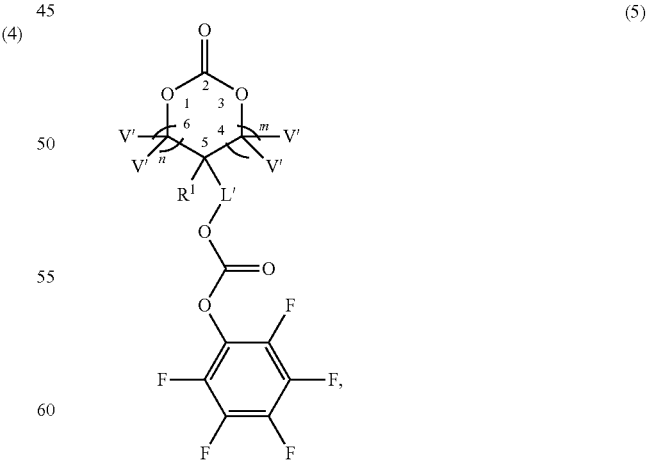

(5)

wherein
m and n are each independently 0 or an integer from 1 to 11, wherein m and n cannot together be 0, and m+n is less than or equal to 11, R[1] is a monovalent radical selected from the group consisting of hydrogen, halides, and alkyl groups comprising 1 to 30 carbons, each V' group is monovalent radical independently selected from the group consisting of hydrogen, halides, pentafluorophenyl carbonate group (—$OCO_2C_6F_5$), alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing V' groups substituted with a pentafluorophenyl carbonate group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

R[1] and L' can together form a first ring comprising 3 to 10 carbons. Each V' can independently form a second ring with a different V' group, with R[1], with L', or combinations thereof, wherein the second ring comprises 3 to 10 carbons.

In an embodiment, the cyclic carbonate compound of formula (5) comprises a single pentafluorophenyl carbonate group. In another embodiment, each V' is hydrogen. In another embodiment, m and n are equal to 1, and R[1] is a monovalent hydrocarbon group comprising 1 to 10 carbons. In another embodiment, R[1] is selected from the group consisting of methyl, ethyl, propyl, 2-propyl, n-butyl, 2-butyl, sec-butyl (2-methylpropyl), t-butyl (1,1-dimethylethyl), n-pentyl, 2-pentyl, 3-pentyl, iso-pentyl, and neo-pentyl.

Even more specific first cyclic carbonate monomers are represented by the general formula (6):

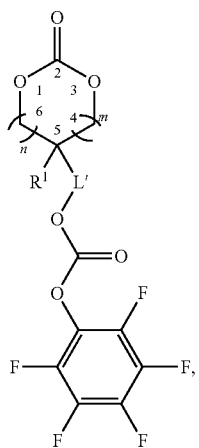

(6)

wherein m and n are each independently 0 or an integer from 1 to 11, wherein m and n cannot together be 0, and m+n is less than or equal to 11, R[1] is a monovalent radical selected from the group consisting of hydrogen, halides, and alkyl groups comprising 1 to 30 carbons, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

R[1] and L' can together form a first ring comprising 3 to 10 carbons. Each V' can independently form a second ring with a different V' group, with R[1], with L', or combinations thereof, wherein the second ring comprises 3 to 10 carbons.

In an embodiment, m and n are each independently 0 or an integer from 1 to 3, wherein m and n together cannot be 0. In another embodiment, m and n are each equal to 1, and R[1] is a monovalent hydrocarbon group comprising 1 to 10 carbons. Exemplary R[1] groups include, for example, methyl, ethyl, propyl, 2-propyl, n-butyl, 2-butyl, sec-butyl (2-methylpropyl), t-butyl (1,1-dimethylethyl), n-pentyl, 2-pentyl, 3-pentyl, iso-pentyl, and neo-pentyl.

In an embodiment, the first cyclic carbonate compound is selected from the group consisting of

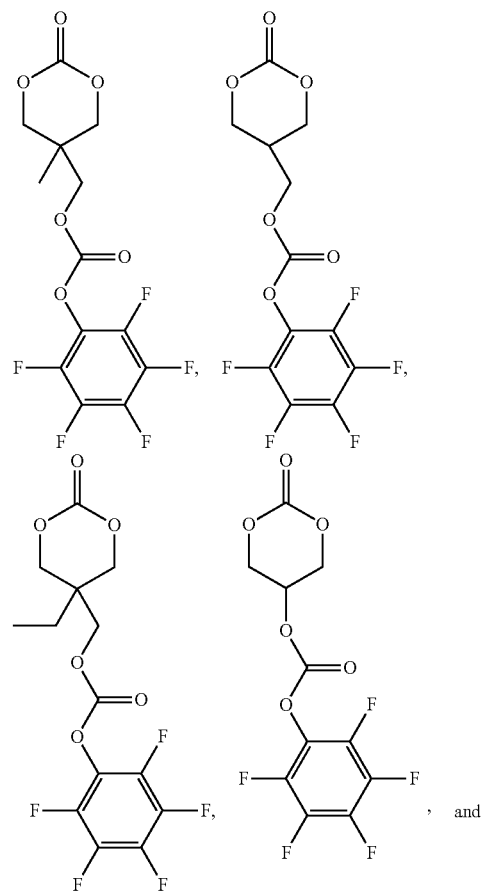

, and

-continued

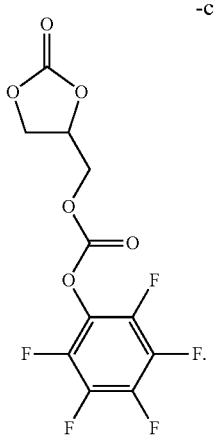

Scheme 5.

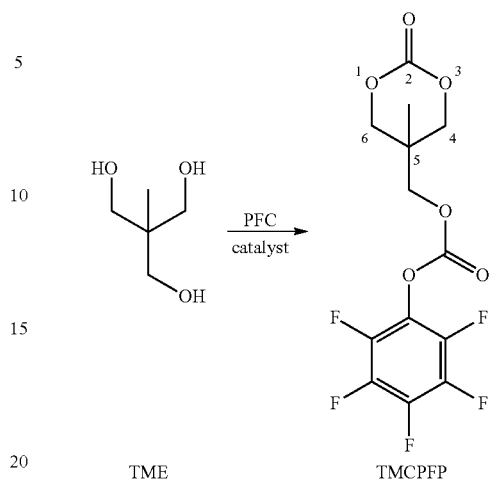

Method 1. Preparation of the First Cyclic Carbonyl Compound

A method (Method 1) of preparing a first cyclic carbonyl compound bearing a pendant pentafluorophenyl carbonate group comprises forming a first mixture comprising bis(pentafluorophenyl) carbonate, a catalyst, an optional solvent, and a precursor compound, the precursor compound comprising i) three or more carbons, ii) a first hydroxy group capable of forming a pentafluorophenyl carbonate in a reaction with bis(pentafluorophenyl) carbonate, and iii) two nucleophilic groups (e.g., the X groups in formula (1) or the X' groups in formula (3)) independently selected from the group consisting of alcohols, amines, and thiols, the two nucleophilic groups capable of forming a cyclic carbonyl group in a reaction with bis(pentafluorophenyl) carbonate. The first mixture is agitated at a temperature effective in forming a first cyclic carbonyl compound. The first cyclic carbonyl compound comprises i) a pendant pentafluorophenyl carbonate group and ii) a cyclic carbonyl moiety selected from the group consisting of cyclic carbonates, cyclic ureas, cyclic carbamates, cyclic thiocarbamates, cyclic thiocarbonates, and cyclic dithiocarbonates.

The formation of the cyclic carbonyl moiety and the pendant pentafluorophenyl carbonate can occur in a single process step under mild conditions.

The precursor compound can comprise more than one pentafluorophenyl carbonate forming hydroxy group and more than two nucleophilic groups capable of forming a cyclic carbonyl group in a reaction with bis(pentafluorophenyl) carbonate. Consequently, the first cyclic carbonyl monomer can comprise more than one cyclic carbonyl moiety and more than one pendant pentafluorophenyl carbonate group. In an embodiment, the first cyclic carbonyl compound comprises one pentafluorophenyl carbonate group. In another embodiment, the first cyclic carbonyl compound comprises one cyclic carbonyl moiety.

In a specific embodiment, a method comprises agitating a first mixture comprising i) a precursor compound comprising three or more carbons and three or more hydroxy groups, ii) bis(pentafluorophenyl) carbonate, and iii) a catalyst, thereby forming a first cyclic carbonate compound comprising a pendant pentafluorophenyl carbonate group.

As a non-limiting example, the preparation of cyclic carbonate compound TMCPFP is illustrated in Scheme 5. TMCPFP is formed by the reaction of the biocompatible precursor compound, tris(hydroxymethyl)ethane (TME), also known as 1,1,1-trimethylolethane, with PFC.

Carbon 5 of the ring is attached to a pendant methylene pentafluorophenyl carbonate group (i.e., —$CH_2OCO_2C_6F_5$) and a pendant methyl group. The reaction can be conducted using about 2 to about 2.5 molar equivalents of PFC, more specifically 2.2 to 2.3 molar equivalents, for each mole of tris(hydroxymethyl)ethane. Generally, 3 moles of pentafluorophenol are produced as a byproduct (not shown) per 2 moles of PFC used. Each theoretical mole of pentafluorophenol byproduct can be recovered in 90% to 100% yield for recycling back to PFC. In an embodiment, the theoretical amount of pentafluorophenol byproduct is quantitatively recovered for recycling back to PFC. TMCPFP is a white, crystalline powder which can be easily handled, manipulated, stored, and shipped.

The use of PFC eliminates the multi-step process using protection/deprotection reactions, eliminates the use of expensive and/or hazardous reagents, and eliminates the multiple wasteful work-ups in the prior art synthetic pathway to cyclic carbonate compounds. By reducing waste, eliminating hazardous reagents, and using recyclable materials, the process improves the overall environmental compatibility of the process of preparing functionalized cyclic carbonate compounds.

Exemplary precursor compounds for preparing cyclic carbonates bearing a pendant pentafluorophenyl carbonate group include but are not limited to triols such as 1,1,1-trimethylol ethane (TME), 1,1,1-trimethylol propane, 1,2,3-propane triol, 2-hydroxymethyl-1,3-propanediol, 2-(hydroxymethyl)-2-methyl-1,3-propane diol, butane-1,2,3-triol, butane-1,2,4-triol, 1,1,1-trimethylol butane; 1,1,1-trimethylol pentane; 1,2,5-pentane triol, 1,1,1-trimethylol hexane, 1,2,3-hexane triol, 1,2,6-hexane triol, cyclohexane-1,2,3-triol, cyclohexane-1,2,4-triol, cyclohexane-1,3,5-triol, 2,5-dimethyl-1,2,6-hexanetriol, 1,1,1-trimethylol heptane, 1,2,3-heptanetriol, 4,5-dideoxy-d-erythro-pent-4-enitol, 3,5,5-trimethyl-2,2-dihydroxymethylhexane-1-ol. Exemplary precursor compounds comprising more than three hydroxy groups include erythritol, pentaerythritol, dipentaerythritol, ditrimethylol propane, diglycerol, and ditrimethylol ethane.

Another challenge in preparing cyclic carbonyl monomers, for example cyclic carbonates from 1,3-diols, is achieving selective ring closure without polymerization, which depends on the nucleophilicity of the leaving group and the catalyst used. Advantageously, the pentafluorophenol byproduct is a weak nucleophile and does not initiate polymerization. In an embodiment, the cyclic carbonyl forming reaction with PFC produces more than 0 to less than 2.0 wt. % of a polymer byproduct derived from the precursor compound, based on the weight of the precursor compound. In another embodiment, the cyclic carbonyl forming reaction with PFC produces no detectable polymer byproduct.

The first mixture comprises a catalyst suitably chosen to activate the nucleophilic hydroxy functional groups and not the electrophilic PFC carbonyl group. Exemplary catalysts include tertiary amines, for example 1,8-bis(dimethylamino) naphthalene, referred to also as PROTON SPONGE, a trademark of Sigma-Aldrich. Still other catalysts include halide salts of Group I elements, particularly lithium (Li), sodium (Na), potassium (K), rubidium (Rb), cesium (Cs), or francium (Fr). In one embodiment the catalyst is CsF.

The catalyst can be present in an amount of 0.02 to 1.00 moles per mole of the precursor compound, more particularly 0.05 to 0.50 moles per mole of the precursor compound, and even more particularly 0.15 to 0.25 moles per mole of the precursor compound.

The first mixture optionally includes a solvent such as tetrahydrofuran, acetonitrile (many other solvents can be used as well), or combinations thereof. When a solvent is present, the concentration of precursor compound in the solvent can be from about 0.01 to about 10 moles per liter, more typically about 0.02 to 0.8 moles per liter, more specifically 0.1 to 0.6 moles per liter, or most specifically 0.15 to 0.25 moles per liter. In one embodiment, the reaction mixture consists of the precursor compound, PFC, a catalyst and a solvent. In one embodiment the solvent is anhydrous.

The first mixture is agitated at a temperature suitable for converting the precursor compound into a first cyclic carbonyl compound. The temperature can be from −20° C. to 100° C., 0° C. to 80° C., 10° C. to 50° C., or more specifically ambient or room temperature, typically 17° C. to 30° C. Optionally, the reaction mixture is agitated under an inert atmosphere. In one embodiment, the temperature is ambient temperature. Care should be taken to avoid an initial mild exotherm during reagent mixing which may lead to the formation of unwanted dimeric carbonate by-products.

Agitation of the first mixture can be conducted for a period of 1 hour to 120 hours, 5 hours to 48 hours, and more specifically 12 hours to 36 hours. In one embodiment, agitation is conducted for 15 to 24 hours at ambient temperature.

The second mixture comprises the first cyclic carbonyl compound comprising the pendant pentafluorophenyl carbonate group and pentafluorophenol byproduct. The first cyclic carbonyl monomer can be isolated using any known method of purification, including distillation, chromatography, extraction, precipitation, and recrystallization. In one embodiment, the first cyclic carbonyl compound is purified by selective precipitation of the pentafluorophenol byproduct or the first cyclic carbonyl monomer from the second mixture. In one variation on selective precipitation, the reaction mixture comprises a first solvent in which the precursor compound, PFC, first cyclic carbonyl monomer and pentafluorophenol byproduct are highly soluble. Upon completion of the reaction to form the first cyclic carbonyl compound, the first solvent is removed by, for example, vacuum distillation, followed by addition of a second solvent suitably chosen to selectively precipitate the pentafluorophenol byproduct or the first cyclic carbonyl compound. In another variation, the first solvent can be selected to facilitate precipitation of the first cyclic carbonyl compound or the pentafluorophenol byproduct from the second mixture as the reaction proceeds. In yet another variation, after removal of the pentafluorophenol byproduct, the first cyclic carbonyl compound is further purified by recrystallization.

The method (Method 1) can further comprise the step of recovering the pentafluorophenol byproduct for recycling. The yield of recovered pentafluorophenol byproduct from the second mixture is about 80% to 100%, more specifically 90% to 100%, based on the theoretical amount of pentafluorophenol byproduct formed. More particularly, the pentafluorophenol byproduct can be quantitatively recovered for recycling back to PFC.

Method 2. Functionalization of the First Cyclic Carbonyl Compound

Also disclosed is a mild method (Method 2) of preparing a second cyclic carbonyl compound from the first cyclic carbonyl compound by selectively reacting the first cyclic carbonyl compound with a nucleophile such as an alcohol, amine, or thiol, without altering the cyclic carbonyl moiety of the first cyclic carbonyl compound, thereby forming a second cyclic carbonyl compound and pentafluorophenol byproduct. In this reaction, the pendant pentafluorophenyl carbonate group is converted to a second functional group selected from the group consisting of carbonates other than pentafluorophenyl carbonate, carbamates, and thiocarbonates. The second functional group can comprise from 1 to 10000 carbons. An optional catalyst can be used with weaker nucleophiles such as alcohols when forming the second cyclic carbonyl compound. Generally, a catalyst is not required for the reaction of a pendant pentafluorophenyl carbonate group with stronger nucleophiles (e.g., primary amines). In an embodiment, the second cyclic carbonyl compound comprises no pentafluorophenyl carbonate groups.

The second cyclic carbonyl compounds can have the general formula (7):

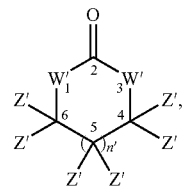

(7)

wherein n' is 0 or an integer from 1 to 10, wherein when n' is 0 carbons labeled 4 and 6 are linked together by a single bond, each W' is a divalent radical independently selected from the group consisting of —O—, —S—, —N(H)— or —N(W")—, wherein each W" group independently represents a monovalent radical selected from the group consisting of alkyl groups comprising 1 to 30 carbons, aryl groups comprising 1 to 30 carbons, and the foregoing W" groups substituted with a second functional group selected from the group consisting of carbonates other than pentafluorophenyl carbonate, carbamates, and thiocarbonates, each Z' group independently represents monovalent radical selected from the group consisting of hydrogen, a second functional group selected from the group consisting of carbonates other than pentafluorophenyl carbonate, carbamates, and thiocarbonates, halides, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, aryl groups comprising 6 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing Z' groups substituted with a second functional group selected from the group consisting of a carbonates other than pentafluorophenyl carbonate, carbamates, and thiocarbonates.

In an embodiment, the second cyclic carbonyl compound comprises no pentafluorophenyl ester group (i.e., —CO$_2$PFP), and no pentafluorophenyl carbonate group (i.e., —OCO$_2$PFP).

A more specific second cyclic carbonyl compound has the general formula (8):

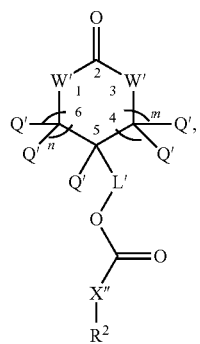

(8)

wherein
m and n are each independently 0 or an integer from 1 to 11, wherein m and n cannot together be 0, and m+n equals an integer from 1 to 11, each W' independently represents divalent radical selected from the group consisting of O, S, NH or NW", wherein each W" group independently represents a monovalent radical selected from the group consisting of alkyl groups comprising 1 to 30 carbons, and aryl groups comprising 1 to 30 carbons, and the foregoing W" groups substituted with a second functional group selected from the group consisting of a carbonates other than pentafluorophenyl carbonate, carbamates, and thiocarbonates, L' represents a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons, each Q' group independently represents a monovalent radical selected from the group consisting of hydrogen, a second functional group selected from the group consisting of a carbonates other than pentafluorophenyl carbonate, carbamates, and thiocarbonates, halides, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, and alkoxy groups comprising 1 to 30 carbons, and any of the foregoing Q' groups substituted with a second functional group selected from the group consisting of a carbonates other than pentafluorophenyl carbonate, carbamates, and thiocarbonates, each X" is a divalent radical independently selected from the group consisting of —O—, —S—, —N(H)—, and —N(R$^3$)—, each R$^2$ and R$^3$ is independently a monovalent radical comprising 1 to 10,000 carbons, and the second cyclic carbonyl compound contains no pentafluorophenyl ester group and no pentafluorophenyl carbonate group.

In an embodiment, each W' is —O— (i.e., the second cyclic carbonyl compound is a cyclic carbonate). In another embodiment, the Q' group attached to the carbon 5 in formula (8) is ethyl or methyl, and all other Q' groups are hydrogen. In another embodiment, carbon 5 in formula (8) is an asymmetric center, and the cyclic carbonyl compound comprises the (R) or (S) isomer in greater than 80% enantiomeric excess.

Even more specific second cyclic carbonyl compounds derived from the first cyclic carbonyl monomer are cyclic carbonates of the general formula (9):

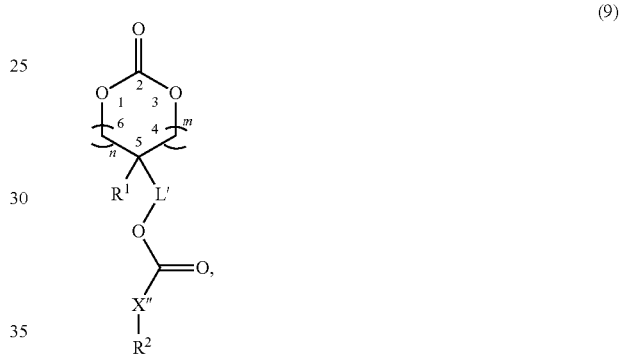

(9)

wherein
m and n are each independently 0 or an integer from 1 to 11, wherein m and n cannot together be 0; and m+n equals an integer from 1 to 11, L' represents a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons;

R$^1$ is a monovalent radical selected from the group consisting of hydrogen, halides, and alkyl groups comprising 1 to 30 carbons;

each X" is a divalent radical independently selected from the group consisting of —O—, —S—, —N(H)—, and —N(R$^3$)—; and each R$^2$ and R$^3$ is independently a monovalent radical comprising 1 to 10,000 carbons; and the second cyclic carbonyl compound contains no pentafluorophenyl ester group and no pentafluorophenyl carbonate group.

The reaction to form the second functional group occurs without disruption of the cyclic carbonyl moiety, in particular the cyclic carbonate moiety, of the first cyclic carbonyl compound. The byproduct of the displacement reaction, pentafluorophenol, can be recovered and recycled, typically in high yield. The second cyclic carbonate compounds are potentially capable of forming ROP polycarbonates and other polymers by ROP methods. The ROP polymers can have unique pendant functionalities and properties due to the wide variety of available materials for the pendant —X"—R² group in formula (7), formula (8), and formula (9).

The method (Method 2) of preparing a second cyclic carbonyl compound comprises agitating a mixture comprising the first cyclic carbonyl compound comprising a pentafluorophenyl carbonate group; an optional solvent; an optional catalyst; and a nucleophile selected from the group consisting of alcohols, amines, and thiols, thereby forming a second cyclic carbonyl monomer and pentafluorophenol byproduct, wherein the second cyclic carbonyl monomer comprises a second functional group selected from the group consisting of carbonates other than pentafluorophenyl carbonate, carbamates, and thiocarbonates formed by a reaction of the pentafluorophenyl carbonate group with the nucleophile.

As one example, TMCPFP can be converted to the corresponding methyl carbonate TMCMe, according to Scheme 6.

Scheme 6.

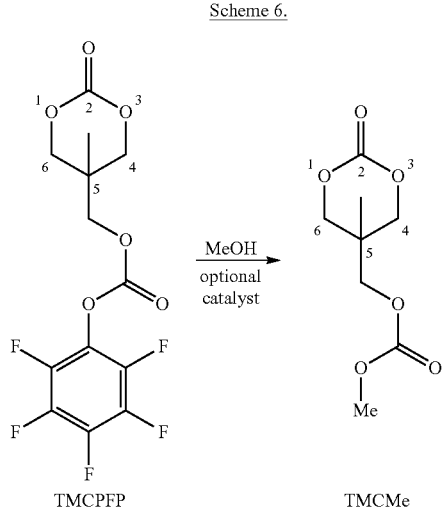

TMCPFP                TMCMe

Non-limiting examples of other alcohols capable of reacting with the pentafluorophenyl carbonate of the first cyclic carbonyl monomer without altering the cyclic carbonyl group include:

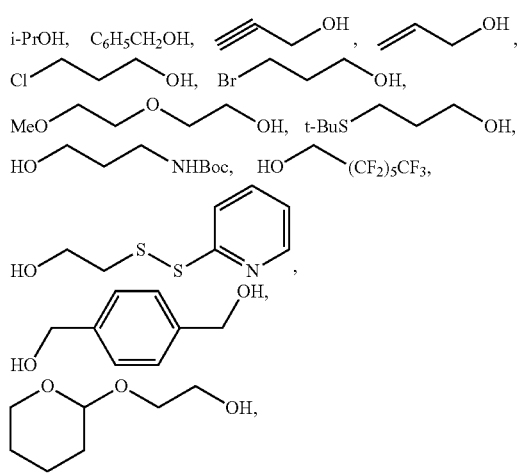

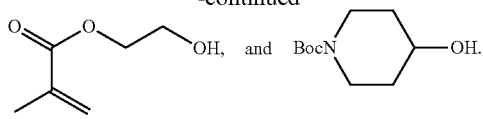

Non-limiting examples of amines capable of reacting with the pentafluorophenyl carbonate of TMCPFP to form a pendant carbamate, without altering the cyclic carbonate group, include:

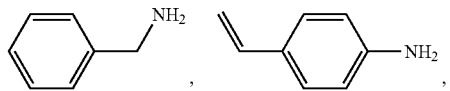

dimethylamine, and
isopropylamine.

Non-limiting examples of thiols capable of reacting with the pendant PFP carbonate to form a pendant thiocarbonate without altering the cyclic carbonyl group include: methane thiol, ethane thiol, phenylthiol, benzyl thiol, and the like.

In general, the efficacy of the substitution reactions proceed in accordance with the nucleophilicity of the nucleophiles. For example, stronger nucleophiles such as primary amines are more effective than weaker nucleophiles such as primary alcohols. In another example, primary and secondary alcohols can be more effective nucleophiles than sterically hindered alcohols such as tert-butanol in a reaction with the pendant pentafluorophenyl carbonate group.

The nucleophile comprising the alcohol, amine, thiol, or combinations thereof can be attached to larger structures including oligomers, polymers, biomacromolecules, particles, and functionalized surfaces. Non-limiting polymeric structures include linear, branched, hyperbranched, cyclic, dendritic, block, graft, star, and other known polymer structures. Non-limiting biomacromolecules include proteins, DNA, RNA, lipids, phospholipids. The particles can have dimensions ranging from less than 1 nanometer to hundreds of micrometers in circular cross-sectional diameter. Non-limiting large particles include silica, alumina, and polymeric resins such as those commonly used for chromatography and functionalized polymeric beads such as those commonly used for solid-phase synthesis. Non-limiting nanoparticles include both organic and inorganic nanoparticles including those functionalized with ligands or stabilizing polymers. Non-limiting organic nanoparticles can include crosslinked polymeric nanoparticles, dendrimers, and star polymers. Non-limiting inorganic nanoparticles include metallic nanoparticles (e.g., gold, silver, other transition metals, and Group 13 to Group 16 metals of the periodic table), oxide nanoparticles (e.g., alumina, silica, hafnia, zirconia, zinc oxide), nitride nanoparticles (e.g., titanium nitride, gallium nitride), sulfide nanoparticles (e.g., zinc sulfide) semiconducting nanoparticles (e.g., cadmium selenide). Non-limiting functionalized surfaces include surfaces functionalized with self-assembled monolayers.

The nucleophile in Method 2 can be a polymeric alcohol. The polymeric alcohol can comprise from 4 to 10000 carbons. In one example, the nucleophile is a polyether alcohol, and the pentafluorophenyl carbonate group of the first cyclic carbonyl compound reacts with the polyether alcohol to form a second cyclic carbonyl containing material comprising a pendant carbonate linked to a hydrophilic polyether chain.

Non-limiting examples of polymeric alcohols include polyether alcohols, such as polyethylene glycol (PEG), and mono end capped polyethylene glycol, such as monomethyl endcapped polyethylene glycol (MPEG):

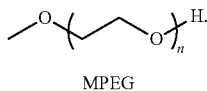

MPEG

Other polymeric alcohols include polypropylene glycol (PPG) and mono endcapped derivatives thereof, such as monomethyl end capped polypropylene glycol (MPPG):

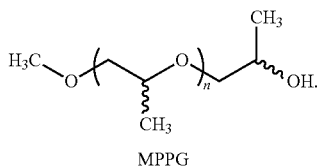

MPPG

Still other polymeric alcohols include poly(alkylene glycols) of formulas (12), (13), and (14) described further below.

Generally, the first mixture (Method 2) is agitated at a temperature of −78° C. to 100° C., more specifically −20° C. to 50° C., and even more specifically −10° C. to 30° C. to form the second cyclic carbonyl compound. In an embodiment, agitation to convert the pentafluorophenyl carbonate to a different carbonate, carbamate, or thiocarbonate is conducted at ambient temperature (herein, 17° C. to 30° C.). The first mixture is agitated for a period of about 1 hour to about 48 hours, more particularly about 20 to 30 hours at the reaction temperature. In an embodiment, the first cyclic carbonyl compound and the second cyclic carbonyl compound are each a cyclic carbonate.

Generally, 1.2 to 1.5 equivalents of the nucleophile with respect to the pentafluorophenyl carbonate are used in the substitution reaction. When a large excess nucleophile is used (e.g., more than 4 equivalents), ring-opening of the cyclic carbonate can occur as a side reaction.

Typically, a solvent is used in Method 2, though a solvent is not required. Depending on the solvent, the pentafluorophenol byproduct can in some instances precipitate directly from the reaction mixture as it is formed. The second cyclic carbonyl compound can be isolated using any known method of purification, including distillation, chromatography, extraction, precipitation, and recrystallization. Generally, however, the second mixture is concentrated under vacuum and the resulting residue is then treated with a second solvent in which the pentafluorophenol byproduct is not soluble, such as methylene chloride. The pentafluorophenol byproduct can then be filtered and recovered for recycling back to PFC. In an embodiment, 90% to 100% of the theoretical pentafluorophenol byproduct is recovered for recycling back to PFC. In one variation, the derived second cyclic carbonate compound can be isolated by washing the organic filtrate with a base such as sodium bicarbonate solution, drying the filtrate with a drying agent such as magnesium sulfate or sodium sulfate, and evaporating the second solvent under vacuum. In a another variation, the second cyclic carbonyl compound is further purified by column chromatography or recrystallization. In this manner the second cyclic carbonyl compound can be obtained in a yield of about 50% to about 100%, more particularly about 70% to 100%, even more particularly about 80% to 100%.

The optional catalyst of Method 2 can be selected from typical catalysts for transesterifications, conversions of carbonates to carbamates, or conversion of carbonates to thiocarbonates. These include organic catalysts and inorganic catalysts, in particular the above described catalysts, and most specifically cesium fluoride. When used in Method 2, the catalyst can be present in an amount of 0.02 to 1.00 moles per mole of the first cyclic carbonyl compound, more particularly 0.05 to 0.50 moles per mole of the first cyclic carbonyl compound, and even more particularly 0.15 to 0.25 moles per mole of the first cyclic carbonyl compound.

In an additional embodiment, Method 1 and Method 2 are performed step-wise in a single reaction vessel, without an intermediate step to isolate the first cyclic carbonyl compound.

The above-described methods provide a controlled process for introducing a wide range of functionality and connectivity into cyclic carbonyl compounds for ring-opening polymerizations. As stated above, the cyclic carbonyl compounds (first and/or second cyclic carbonyl compounds) can be formed in isomerically pure form, or as racemic mixtures.

More specific second cyclic carbonyl compounds include but are not limited to the following cyclic carbonate compounds:

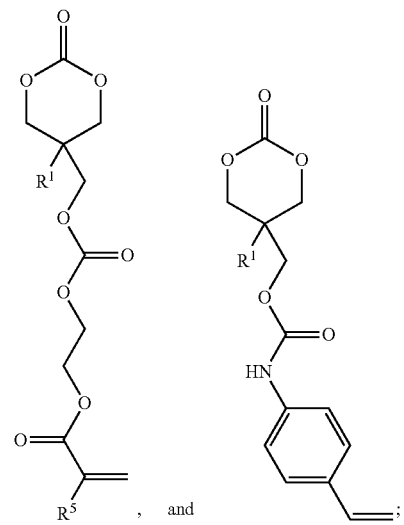

wherein $R^1$ is a monovalent radical selected from the group consisting of hydrogen, halides, and alkyl groups comprising 1 to 30 carbons, and $R^5$ is a monovalent radical selected from the group consisting of hydrogen, halides, alkyl groups comprising 1 to 20 carbons, fluorinated alkyl groups comprising 1 to 20 carbons, and acetoxy groups.

Method 3. Ring Opening Polymerization

Further disclosed are ROP polymers obtained by a nucleophilic ring opening polymerization of the above described first and second cyclic carbonyl compounds. The ROP polymer comprises a chain fragment derived from the nucleophilic initiator for the ROP polymerization, and a first polymer chain linked to the chain fragment. The chain fragment is also referred to herein as the initiator fragment. The initiator fragment comprises at least one oxygen, nitrogen, and/or sulfur backbone heteroatom, which is a residue of a respective alcohol, amine, or thiol nucleophilic initiator group of the ROP initiator. The backbone heteroatom is linked to the first end unit of the first polymer chain grown therefrom. A second end unit of the first polymer chain can be a living end unit capable of initiating additional ring opening polymerization, if desired. A living second end unit comprises a nucleophilic group selected from the group consisting of hydroxy group, primary amines, secondary amines, and thiol group. Alternatively, the second end unit can be endcapped to impart stability to the ROP polymer, as described further below.

It is understood that the initiator fragment has a different structure than the first end unit of each ROP polymer chain connected thereto.

The ROP initiator can comprise one or more independently chosen alcohol, amine, or thiol nucleophilic initiator groups. Each nucleophilic initiator group can potentially initiate a ring opening polymerization. Likewise, the initiator fragment comprises at least one backbone heteroatom derived from a nucleophilic initiator group. Each one of the backbone heteroatoms that is derived from a nucleophilic initiator group is linked to a ROP polymer chain grown therefrom. Thus, an initiator comprising n nucleophilic initiator groups can potentially initiate formation of n independent ROP polymer chains, where n is an integer equal to or greater than 1. As a non-limiting example, a dinucleophilic initiator comprising two hydroxy groups can initiate ring opening polymerization at each hydroxy group. The product ROP polymer comprises an initiator fragment linked to two ROP polymer chains through the two backbone oxygens derived from the hydroxy initiator groups.

The ROP polymer comprises at least one ROP polymer chain, referred to as the first polymer chain. The first polymer chain can comprise a homopolymer, random copolymer, block copolymer, or combinations of the foregoing polymer types. The first polymer chain comprises a first repeat unit comprising a backbone functional group selected from the group consisting of carbonate, urea, carbamate, thiocarbamate, thiocarbonate, and dithiocarbonate. The first repeat unit further comprises a tetrahedral backbone carbon. In an embodiment, the tetrahedral backbone carbon is linked to a first side chain comprising a pendant pentafluorophenyl carbonate. In another embodiment, the tetrahedral backbone carbon is linked to a first side chain comprising a pendant pentafluorophenyl carbonate, and to a second side chain selected from the group consisting of hydrogen, halides, and alkyl groups comprising 1 to 30 carbons (e.g., the $R^1$ group as described in formulas (5) and (6)).

In the following non-limiting examples, R'—XH is a mono-functional nucleophilic initiator for ring opening polymerization. R'—XH comprises a monovalent initiator group —XH, wherein X is a divalent group selected from the group consisting of —O—, —NH—, —NR"—, and —S—. No restriction is placed on the structure of R' or R" with the proviso that the ring opening polymerization produces a useful ROP polymer.

When formed from a first cyclic carbonyl compound, the ROP polymer comprises a pendant pentafluorophenyl carbonate group and is referred herein as the first ROP polymer. As one example, the nucleophilic ring opening polymerization of a first cyclic carbonyl monomer of formula (2) initiated by R'—XH produces a first ROP polymer of formula (2A), which comprises a first polymer chain and an initiator fragment R'—X—.

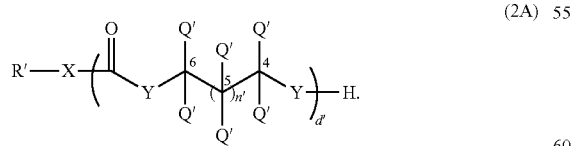

(2A)

Initiator fragment R'—X— is linked to the carbonyl of the first end unit of the first polymer chain through the oxygen, nitrogen or sulfur heteroatom of the X group. A second end unit of the first polymer chain is a living end unit (i.e., —Y—H in formula (2A)), wherein —Y—H is a nucleophilic group selected from the group consisting of hydroxy group, primary amine groups, secondary amine groups, and thiol group. Y, Q', and n' are defined as above under formula (2); thus, at least one of the Q' groups and/or Q" groups (of the Y groups) comprises a pendant pentafluorophenyl carbonate group (—OCO$_2$C$_6$F$_5$). The subscript d' is an integer from 1 to 10000. The repeat unit

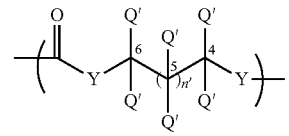

comprises a backbone functional group selected from the group consisting of carbonate, ureas, carbamates, thiocarbamates, thiocarbonate, and dithiocarbonate, determined by the independent selection of each Y group. The first repeat unit further comprises tetrahedral backbone carbons labeled 4, 5 and 6. Each of these backbone carbons can be linked to an independent first side chain Q' group, which can comprise a pentafluorophenyl carbonate group. Further, each of these tetrahedral backbone carbons can be linked to an optional independent second side chain Q' group, as defined above under formula (2).

In another example, the nucleophilic ring opening polymerization of a first cyclic carbonyl monomer of formula (4), initiated by R'—XH, produces a first ROP polymer of formula (4A), which comprises a first polymer chain and an initiator fragment R'-X-:

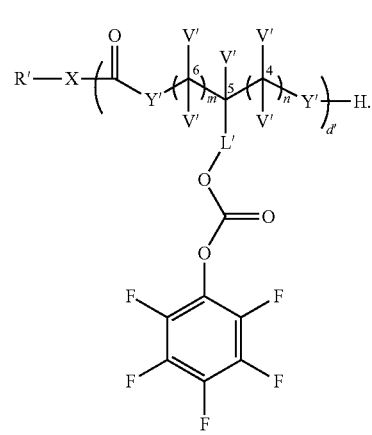

(4A)

As above, the initiator fragment R'-X- is linked to the carbonyl of the first end unit of the first polymer chain by the oxygen, nitrogen or sulfur heteroatom of the X group. Y', L', V', n and m are defined as above under formula (4). The subscript d' is an integer from 1 to 10000. The repeat unit

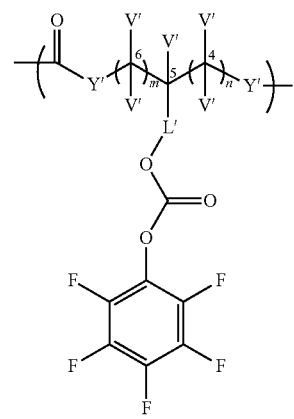

comprises a backbone functional group selected from the group consisting of carbonate, ureas, carbamates, thiocarbamates, thiocarbonate, and dithiocarbonate, determined by the independent selection of each Y' group. Tetrahedral backbone carbon labeled 5 is linked to a first side chain comprising a pentafluorophenyl carbonate group. Tetrahedral backbone carbon labeled 5 can optionally be linked to an independent second side chain V' group, as defined above under formula (4).

In another example, the nucleophilic ring opening polymerization of a first cyclic carbonyl monomer of formula (5), initiated by R'—XH, produces a polycarbonate chain of formula (5A), which comprises a first polymer chain comprising a polycarbonate backbone and an initiator fragment R'-X-:

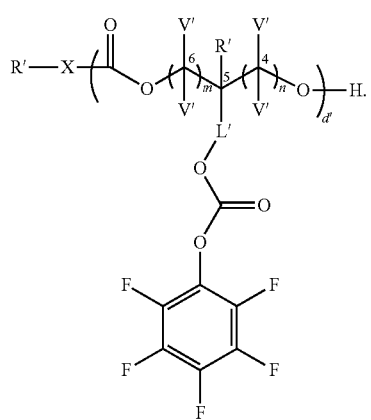
(5A)

Initiator fragment R'-X- is linked by the oxygen, nitrogen or sulfur heteroatom of the X group to the carbonyl of the first end unit of the polycarbonate chain. $R^1$, L', V', m and n are defined as above under formula (5). The subscript d' is an integer from 1 to 10000. The repeat unit

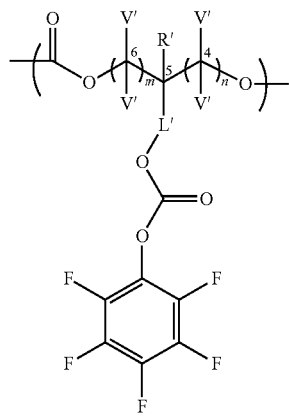

comprises a backbone carbonate group. Tetrahedral backbone carbon labeled 5 is linked to a first side chain comprising a pentafluorophenyl carbonate group, and to a second side chain R' defined above under formula (5). Tetrahedral backbone carbons labeled 4 and 6 can independently be linked to independent first and second side chain V' groups, as described above under formula (5).

In another example, the nucleophilic ring opening polymerization of a first cyclic carbonyl monomer of formula (6), initiated by R'—XH, produces a ROP polycarbonate of formula (6A), which comprises a first polycarbonate chain and an initiator fragment R'-X-:

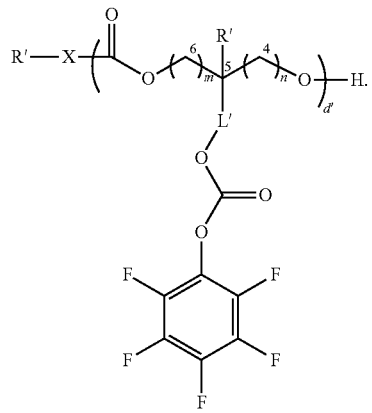
(6A)

Initiator fragment R'-X- is linked by the oxygen, nitrogen or sulfur heteroatom of the X group to the carbonyl of the end unit of the polycarbonate chain. $R^1$, L', m and n are defined as above under formula (6). The subscript d' is an integer from 1 to 10000. The repeat unit

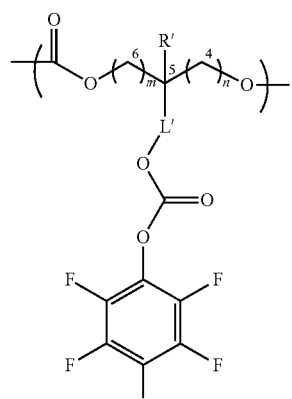

comprises a backbone carbonate group. Tetrahedral backbone carbon labeled 5 is linked to a first side chain comprising a pentafluorophenyl carbonate group, and to a second side chain R' as defined above under formula (6).

The ROP polymer can comprise two or more linked polymer chains. Additionally, each polymer chain can be a homopolymer of a respective first repeat unit, or a copolymer comprising a second repeat unit, the second repeat unit comprising a second backbone functional group selected from the group consisting of ester, carbonate, urea, carbamate, thiocarbamate, thiocarbonate and dithiocarbonate, which is derived from a cyclic carbonyl comonomer. The first polymer chain can be a random copolymer or a block copolymer comprising the first and second repeat units.

Similar considerations apply to ROP polymers prepared from a second cyclic carbonyl compound, except that the ROP polymer chain does not comprise a pentafluorophenyl carbonate group or a pentafluorophenyl ester group. Instead, the ROP polymer comprises a repeat unit comprising a side chain comprising a carbonate group other than pentafluorophenyl carbonate, carbamate group, or thiocarbonate group derived from the pendant pentafluorophenyl carbonate group of the first cyclic carbonyl monomer.

The first and/or second cyclic carbonyl compounds can undergo ring-opening polymerization (ROP) to form biodegradable polymers having different tacticities. Atactic, syndiotactic and isotactic forms of the polymers can be produced that depend on the cyclic monomer(s), its isomeric purity, and the polymerization conditions.

The ring opening polymerization (ROP) of the first cyclic carbonyl compound can occur with substantial retention of the pendant pentafluorophenyl carbonate group in the product ROP polymer, which is also referred to as the first ROP polymer. The first ROP polymer comprises at least one repeat unit comprising a side chain comprising a reactive pentafluorophenyl carbonate group. The first ROP polymer further comprises a backbone segment derived from the ring opening of the first cyclic carbonyl compound, the backbone segment selected from the group consisting of polycarbonates, polycarbamates, polyureas, polythiocarbamates, polythiocarbonates, and polydithiocarbonates. The first ROP polymer can further comprise a polyester backbone segment when a cyclic ester (lactone) comonomer is used in the ring opening polymerization. Each of these repeat structures is shown in Table 2. The R group in Table 2 is a backbone fragment formed by the carbons of the ring containing the cyclic carbonyl group.

TABLE 2

| Polyester | 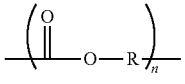 |
| Polycarbonate | 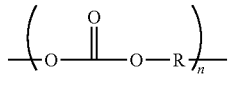 |
| Polyurea | 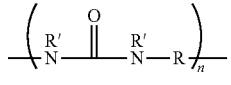 |
| Polycarbamate | 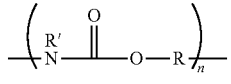 |
| Polythiocarbamate | 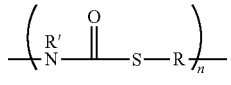 |
| Polythiocarbonate | 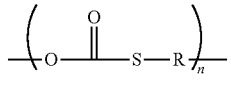 |
| Polydithiocarbonate | 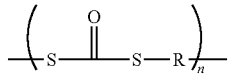 |

The method (Method 3) comprises forming a first mixture comprising the first cyclic carbonyl compound comprising a pendant pentafluorophenyl carbonate group, a catalyst, an initiator, an accelerator, and an optional solvent. The first mixture is then agitated with optional heating to effect ring opening polymerization of the first cyclic carbonyl compound, thereby forming a second mixture containing a biodegradable ROP polymer, while retaining the pendant pentafluorophenyl carbonate group. The ROP polymer comprises a first polymer chain, the first polymer chain comprising a first repeat unit, the first repeat unit comprising a side chain comprising a pendant pentafluorophenyl carbonate group. In a specific embodiment, the side chain has the structure:

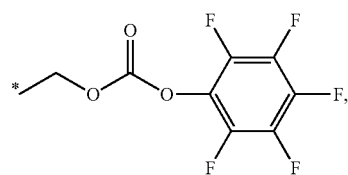

wherein the starred bond is linked to a backbone carbon of the biodegradable first ROP polymer. In another embodiment, the first repeat unit of the first ROP polymer comprises a tetrahedral backbone carbon, the tetrahedral backbone carbon linked to i) a first side chain comprising a pentafluorophenyl carbonate group, and ii) a second side chain group comprising a monovalent hydrocarbon radical. The monovalent hydrocarbon radical can comprise from 1 to 30 carbons. More specifically, the monovalent hydrocarbon radical is selected from the group consisting of methyl, ethyl, propyl, butyl and pentyl.

In an embodiment, the polymer retains at least 50%, and more specifically at least 75%, and even more specifically at least 90% of the pentafluorophenyl carbonate groups relative to the repeat units derived from the first cyclic carbonyl compounds.

As a non-limiting example, TMCPFP undergoes ring opening polymerization in the presence of a suitable catalyst and nucleophilic initiator benzyl alcohol to form a first ROP polymer, a polycarbonate (Scheme 7), wherein BnO is an initiator fragment.

Scheme 7.

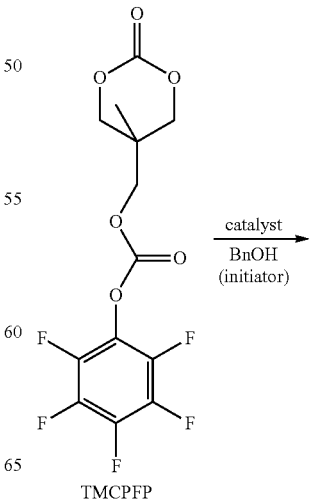

TMCPFP

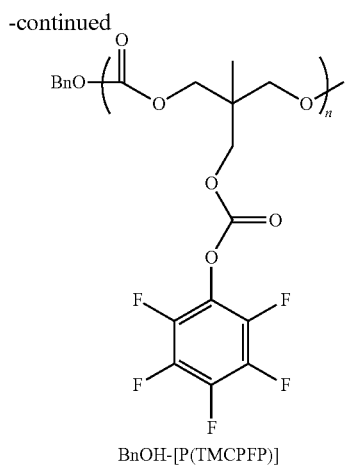

BnOH-[P(TMCPFP)]

In the naming notation used herein for a ROP polymer, I-[P (Monomer 1, Monomer 2, etc.)]$_w$, "I" is the initiator, "[P( )]" indicates a polymer chain formed by ring opening polymerization of one or more cyclic carbonyl compounds listed in the parentheses, and w is the number of nucleophilic initiator groups of the initiator. For example, if the initiator is benzyl alcohol, the initiator fragment is a benzyloxy group (BnO), and the name of the ROP homopolymer is BnOH—[P(TMCPFP)]. The ROP polymer can be prepared under mild conditions to achieve high molecular weight and low polydispersity. Additionally, the ROP polymer can have substantially no metal contaminant when prepared with an organocatalyst. The wide utility and ease of manufacture of the first cyclic carbonyl compounds (and their corresponding ROP polymers) makes these monomers considerably more useful than similar compounds comprising an acyl chloride group or a succinimidyl ester group. The efficient method of forming ROP polymers having an active pentafluorophenyl carbonate side chain group represents a significant advancement in the state of the art in preparing functionalized ROP polymers.

The first mixture can comprise comonomers, including but not limited to comonomers comprising a functional group selected from the group consisting of cyclic ethers, cyclic esters, cyclic carbonates, cyclic ureas, cyclic carbamates, cyclic thioureas, cyclic thiocarbonates, and cyclic dithiocarbonates. Exemplary comonomers include: L-lactide, D-lactide, DL-lactide, beta-butyrolactone, delta-valerolactone, epsilon-caprolactone, trimethylene carbonate, methyl 5-methyl-2-oxo-1,3-dioxane-5-carboxylate, ethyl 5-methyl-2-oxo-1,3-dioxane-5-carboxylate, and other derivatives of MTC-OH. These and other examples of cyclic carbonyl comonomers are listed in Table 3.

TABLE 3

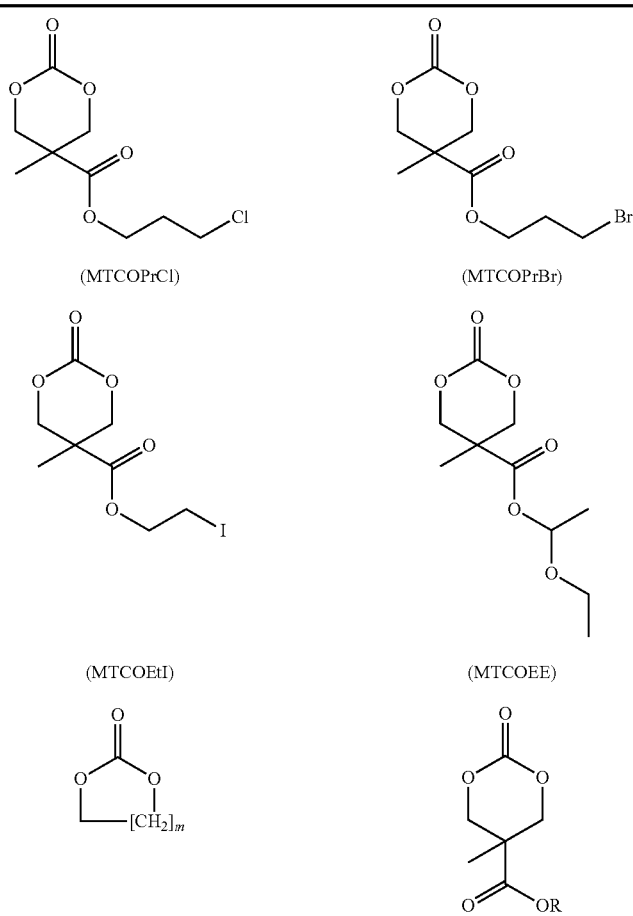

m = 1, Trimethylene carbonate (TMC)
m = 2, Tetramethylene carbonate (TEMC)
m = 3, Pentamethylene carbonate (PMC)

R = hydrogen (MTCOH)
R = methyl (MTCOMe)
R = t-butyl (MTCO$^t$Bu)
R = ethyl (MTCOEt)

TABLE 3-continued
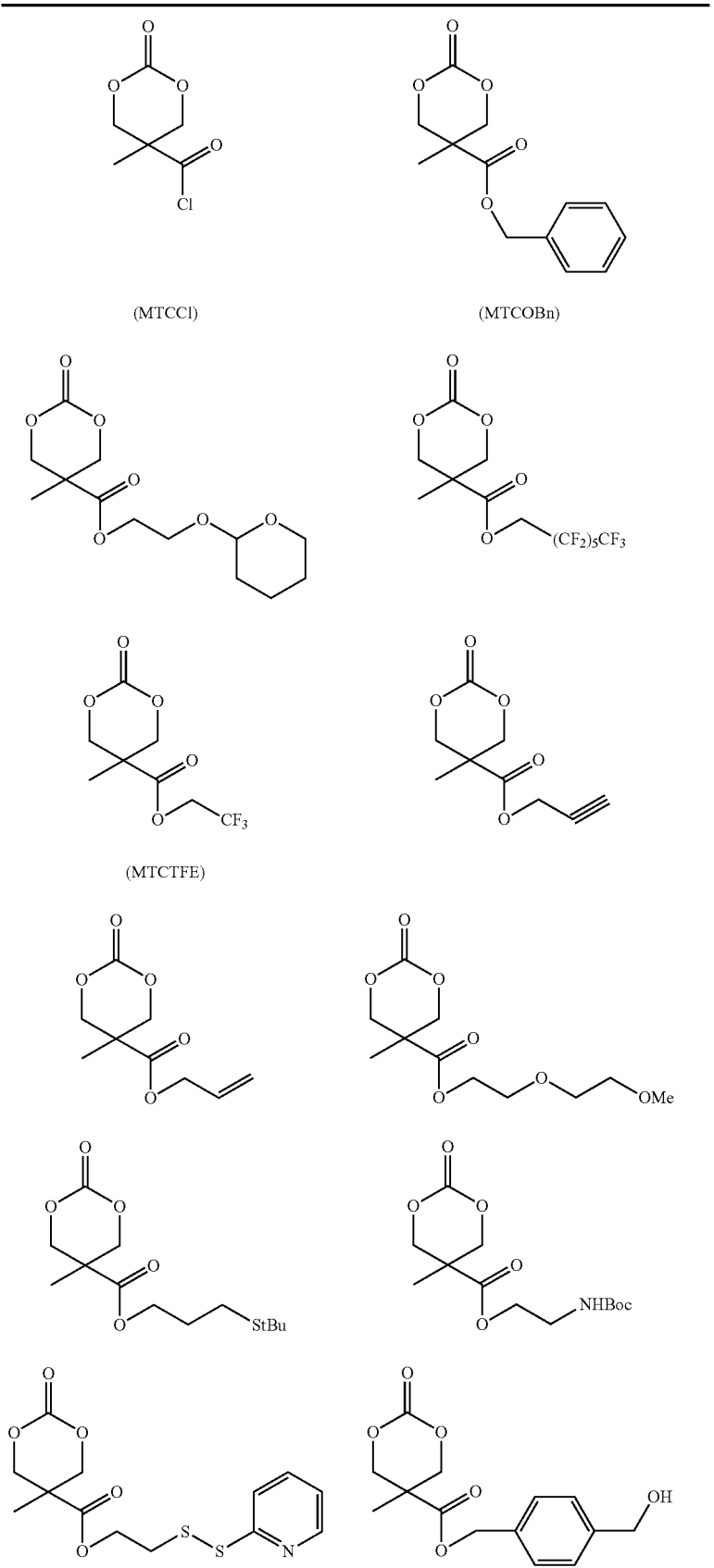

TABLE 3-continued
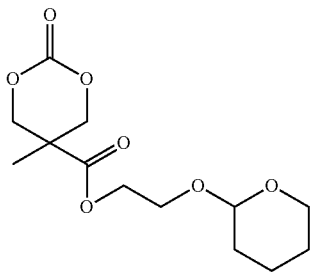 [SMILES: CC1(C(=O)OCCOC2CCCCO2)COC(=O)OC1]
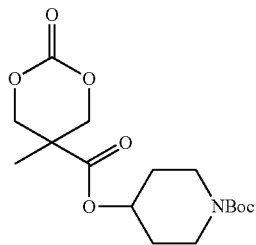 [SMILES: CC(C)(C)OC(=O)N1CCC(OC(=O)C2(C)COC(=O)OC2)CC1]
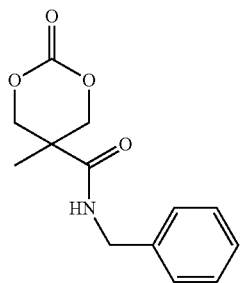 [SMILES: CC1(C(=O)NCc2ccccc2)COC(=O)OC1]
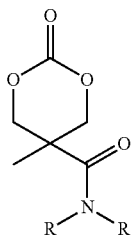
R = methyl
R = iso-propyl
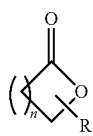
R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)
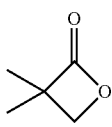
Pivalolactone
(PVL)
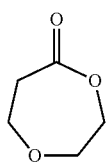
1,5-Dioxepan-2-one
(DXO)
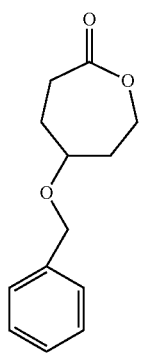 [SMILES: O=C1CCC(OCc2ccccc2)CCO1]
5-(Benzyloxy)oxepan-2-one
(BXO)

TABLE 3-continued
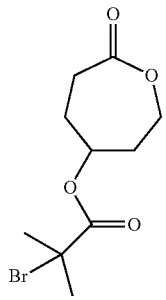
7-Oxooxepan-4-yl 2-bromo-2-
methylpropanoate
(BMP-XO)
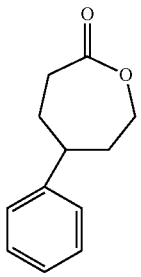 [SMILES: O=C1CCC(c2ccccc2)CCO1]
5-Phenyloxepan-2-one
(PXO)
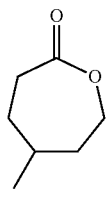
5-Methyloxepan-2-one
(MXO)
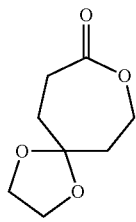 [SMILES: O=C1CCC2(CCO1)OCCO2]
1,4,8-Trioxa(4,6)spiro-9-undecane
(TOSUO)
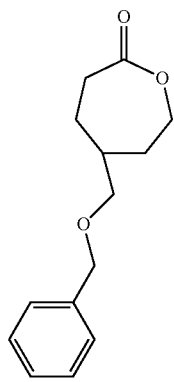 [SMILES: O=C1CCC(COCc2ccccc2)CCO1]
5-(Benzyloxymethyl)oxepan-2-one
(BOMXO)
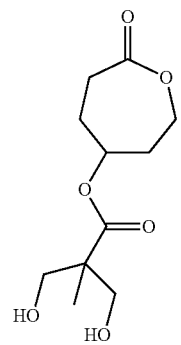
7-Oxooxepan-4-yl 3-hydroxy-2-
(hydroxymethyl)-2-methylpropanoate
(OX-BHMP)

TABLE 3-continued

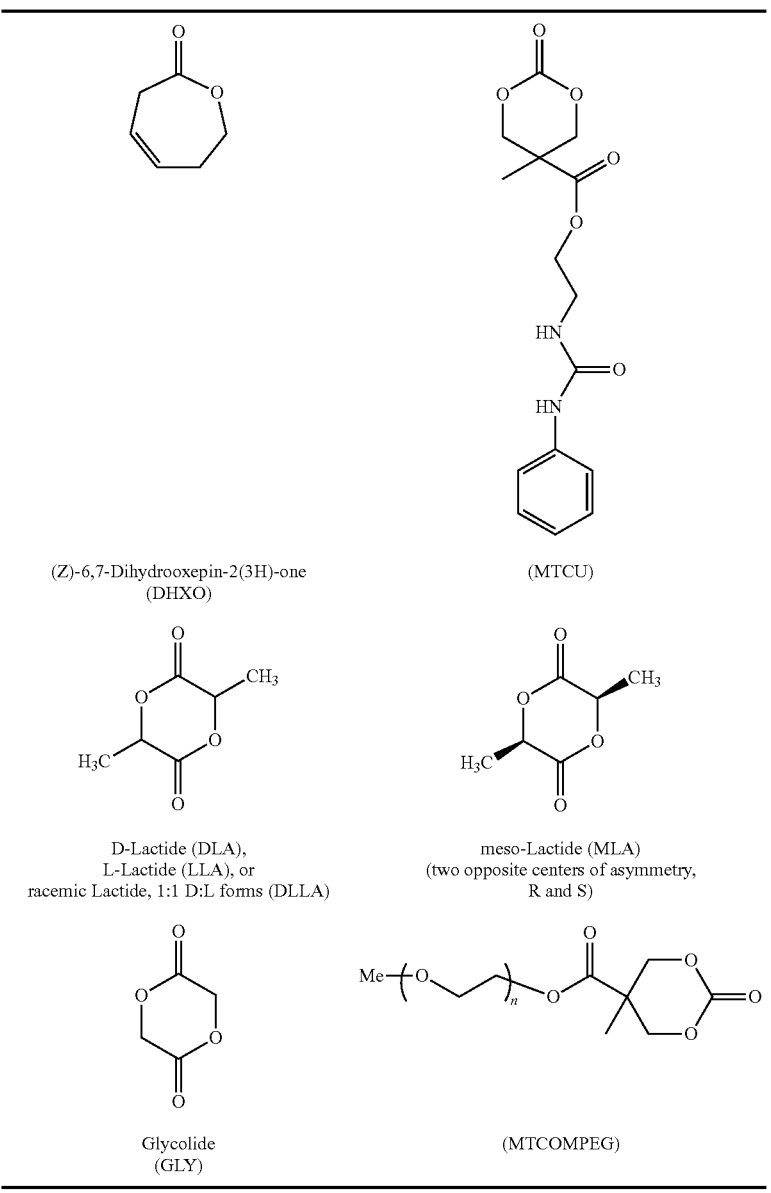

The ring opening polymerization is generally conducted in a reactor under anhydrous conditions and with an inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from 20° C. to 250° C. Generally, the reaction mixture is heated at atmospheric pressure for 0.5 to 72 hours to effect polymerization. Subsequently, additional cyclic carbonyl compound and catalyst can be added to the second mixture to effect block polymerization if desired.

Exemplary organometallic ROP catalysts include tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Organocatalysts for the ROP Polymerization.

Other ROP catalysts include metal-free organocatalysts, defined herein as a catalyst having none of the following metals in the chemical formula of the organocatalyst: beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. This exclusion includes ionic and non-ionic forms of the foregoing metals. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Organocatalysts can provide a platform to polymers having controlled, predictable molecular weights and narrow polydispersities, and minimal metal contamination. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, guanidines, and fluoroalcohols (such as mono- and bis-hexafluoroisopropanol compounds).

More specific metal-free organocatalysts for the ROP polymerization of the first cyclic monomer include N-(3,5-trifluoromethyl)phenyl-N'-cyclohexyl-thiourea (TU):

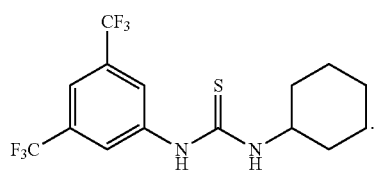

(TU)

Another metal-free organocatalyst comprises at least one 1,1,1,3,3,3-hexafluoropropan-2-ol-2-yl (HFP) group. Singly-donating hydrogen bond catalysts have the formula (10):

$$R^2\!\!-\!\!C(CF_3)_2OH \quad (10),$$

wherein $R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 4.

TABLE 4

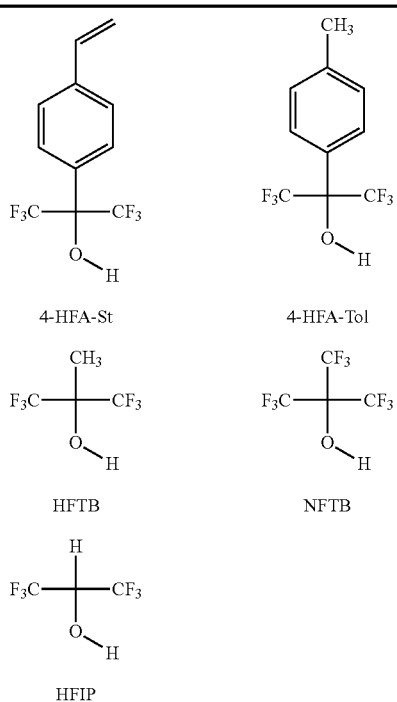

Doubly-donating hydrogen bonding catalysts have two HFP groups, represented by the general formula (11):

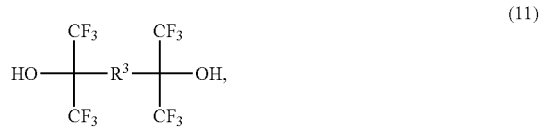

wherein $R^3$ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (11) include those listed in Table 5. In a specific embodiment, $R^2$ is an arylene or substituted arylene group, and the HFP groups occupy positions meta to each other on the aromatic ring.

TABLE 5

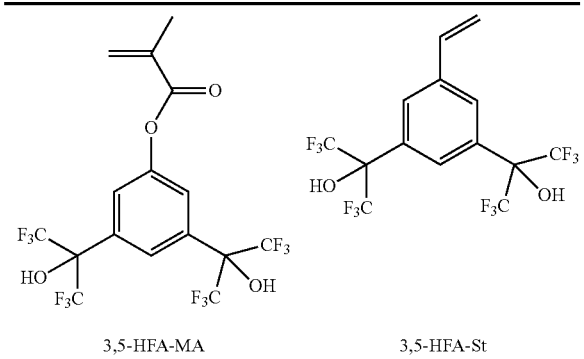

TABLE 5-continued

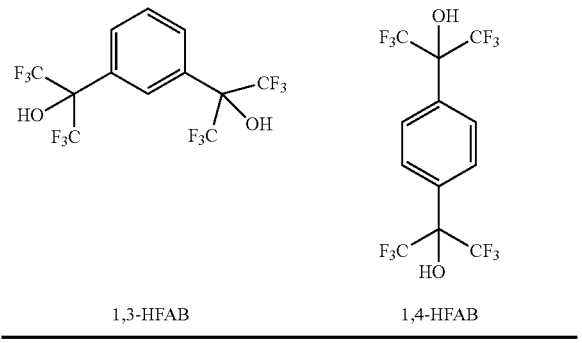

1,3-HFAB        1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

In particular, catalysts bearing 1,3-bis-HFP aromatic groups (such as 1,3-HFAB) were found to be efficient in catalyzing the ROP of TMCPFP without concomitant reaction of the pentafluorophenyl carbonate side chain.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizeable HFP-containing monomers may be found in: Ito et al., *Polym. Adv. Technol.* 2006, 17(2), 104-115; Ito et al., *Adv. Polym. Sci.* 2005, 172, 37-245; Ito et al., US20060292485; Maeda et al., WO2005098541; Allen et al., US20070254235; and Miyazawa et al., WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003; M. Delgado and K. D. Janda "Polymeric Supports for Solid Phase Organic Synthesis," *Curr. Org. Chem.* 2002, 6(12), 1031-1043; A. R. Vaino and K. D. Janda "Solid Phase Organic Synthesis: A Critical Understanding of the Resin", *J. Comb. Chem.* 2000, 2(6), 579-596; D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377; and T. J. Dickerson et al., "Soluble Polymers as Scaffold for Recoverable Catalysts and Reagents," *Chem. Rev.* 2002, 102(10), 3325-3343. Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

The ROP reaction mixture comprises at least one catalyst and, when appropriate, several catalysts together. The ROP catalyst is added in a proportion of 1/20 to 1/40,000 moles relative to the cyclic compounds, and preferably of 1/1,000 to 1/20,000 moles.

Accelerators for ROP Polymerizations.

A nitrogen base can serve as catalyst or as an optional accelerator for a catalyst in a ring opening polymerization. Exemplary nitrogen bases are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl) imidazol-2-ylidene (Im-2), 1,3-bis(2,6-di-1-propylphenyl (imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis (2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 6.

TABLE 6

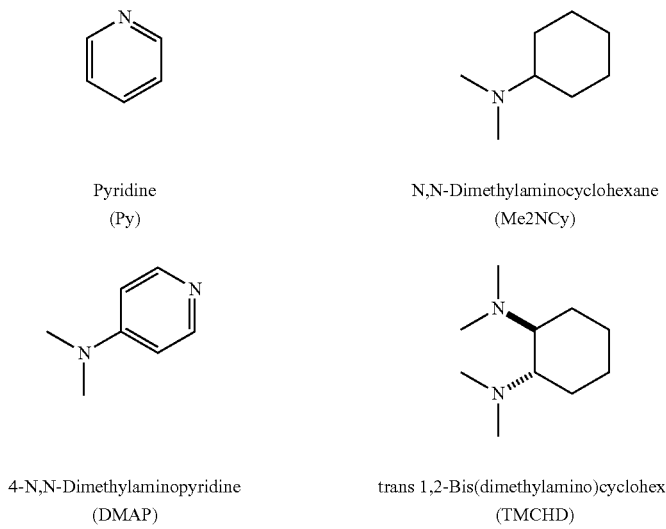

Pyridine (Py)

N,N-Dimethylaminocyclohexane (Me2NCy)

4-N,N-Dimethylaminopyridine (DMAP)

trans 1,2-Bis(dimethylamino)cyclohexane (TMCHD)

TABLE 6-continued
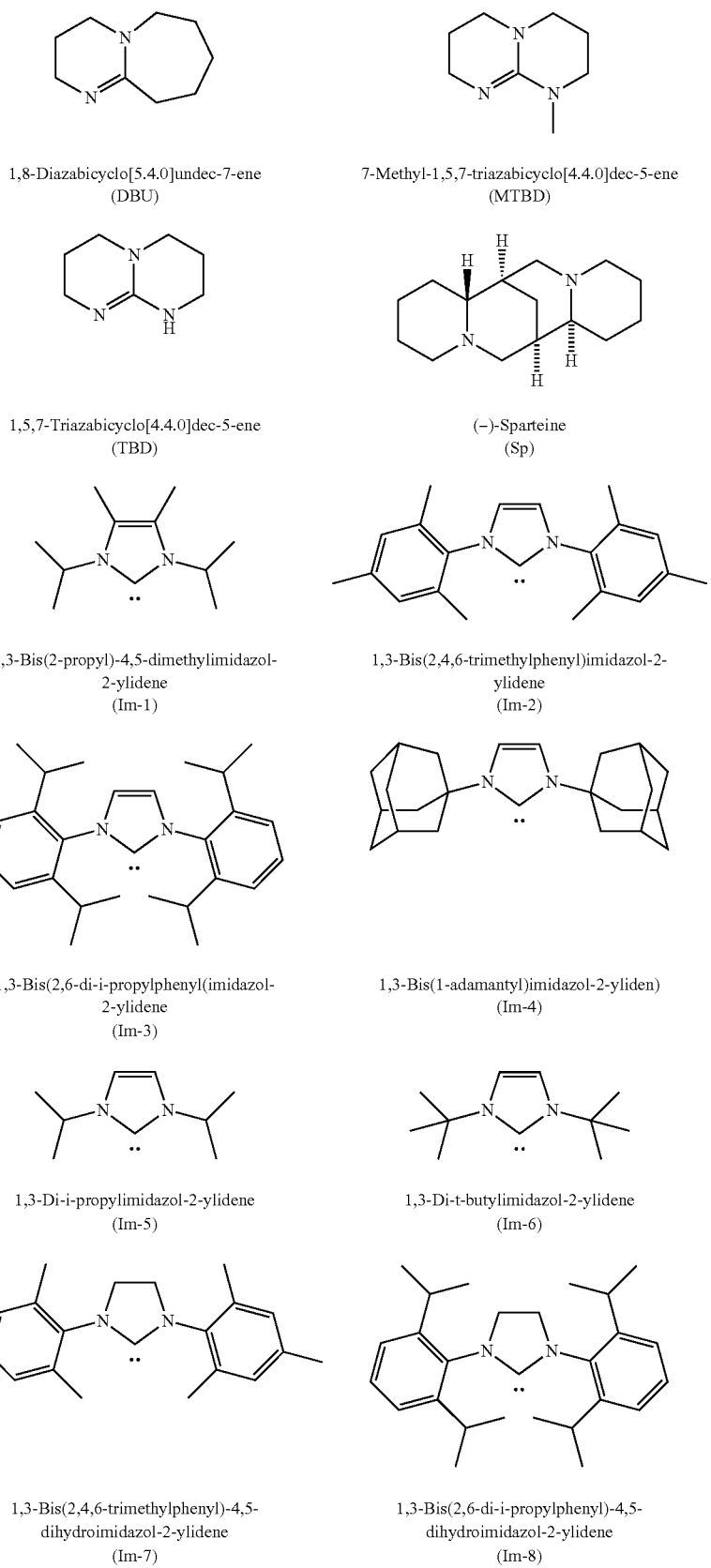

In an embodiment, the accelerator has two or three nitrogens, each capable of participating as a Lewis base, as for example in the structure (−)-sparteine. Stronger bases generally improve the polymerization rate. In some instances, the nitrogen base is the sole catalyst in a ring opening polymerization, such as 1,8-diazabicyclo[5.4.0]undec-7-ene (DBU).

Initiators for the ROP Polymerization.

The ROP reaction mixture also comprises an initiator. As stated above, initiators generally include nucleophiles (e.g., alcohols, amines, and thiols). The initiator can be monofunctional, difunctional or multifunctional such as dendritic, polymeric or related architectures. Monofunctional initiators can include nucleophiles with protected functional groups that include thiols, amines, acids and alcohols. A typical initiator is phenol or benzyl alcohol.

More particularly, the initiator for the ring opening polymerization of the first cyclic carbonyl compound bearing a pendant pentafluorophenyl carbonate is an alcohol. The alcohol initiator can be any suitable alcohol, including mono-alcohol, diol, triol, or other polyol, with the proviso that the choice of alcohol does not adversely affect the polymerization yield, polymer molecular weight, and/or the desirable mechanical and physical properties of the resulting first ROP polymer. The alcohol can be multi-functional comprising, in addition to one or more hydroxy groups, a halide, an ether group, an ester group, an amide group, or other functional group. Additional exemplary alcohols include methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, alcohol functionalized branched polymers derived from branched alcohols, or a combination thereof. Monomeric diol initiators include ethylene glycols, propylene glycols, hydroquinones, and resorcinols. An example of a diol initiator is BnMPA, derived from 2,2-dimethylol propionic acid, a precursor used in the preparation of cyclic carbonate monomers.

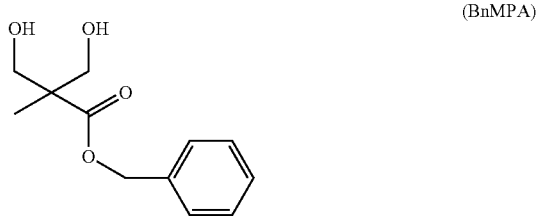 [SMILES: CC(CO)(CO)C(=O)OCc1ccccc1]
(BnMPA)

More particular polymeric alcohol initiators are polyether alcohols, such as a poly(alkylene glycol) or a mono end capped poly(alkylene glycol) which includes but is not limited to poly(alkylene glycol)s and mono end capped poly(alkylene glycol)s. Such initiators serve to introduce a main chain hydrophilic first block into the resulting first ROP polymer. A second block of the ROP polymer comprises a living chain segment comprising a side chain pentafluorophenyl carbonate group, the living chain segment formed by ring opening polymerization of a first cyclic carbonyl compound.

The polyether alcohol can be a poly(alkylene glycol) of the general formula (12):

$$HO\text{—}[C(R^7)_2(C(R^7)_2)_{a'}C(R^7)_2O]_n\text{—}H \quad (12),$$

Wherein a' is 0 to 8, n is an integer from 2 to 10000, and each $R^7$ is independently a monovalent radical consisting of hydrogen and an alkyl group of 1 to 30 carbons. Thus, the ether repeat unit comprises 2 to 10 backbone carbons between each backbone oxygen. More particularly, the poly(alkylene glycol) can be a mono end capped poly(alkylene glycol), represented by the formula (13):

$$R^8O\text{—}[C(R^7)_2(C(R^7)_2)_{a'}C(R^7)_2O]_n\text{—}H \quad (13),$$

wherein $R^8$ is a monovalent hydrocarbon radical comprising 1 to 20 carbons.

As non-limiting examples, the polyether alcohol can be a poly(ethylene glycol) (PEG), having the structure HO—[$CH_2CH_2O$]$_n$—H, wherein the ether repeat unit $CH_2CH_2O$ (shown in the brackets) comprises two backbone carbons linked to a backbone oxygen. The polyether alcohol can also be a polypropylene glycol) (PPG) having the structure HO—[$CH_2CH(CH_3)O$]$_n$—H, where the ether repeat unit $CH_2CH(CH_3)O$ comprises two backbone carbons linked to a backbone oxygen with a methyl side-chain. An example of mono end capped PEG is the commercially available mono methyl end capped PEG (MPEG), wherein $R^8$ is a methyl group. Other examples include poly(oxetane), having the structure HO—[$CH_2CH_2CH_2O$]$_n$—H, and poly(tetrahydrofuran), having the structure HO—[$CH_2(CH_2)_2CH_2O$]$_n$—H.

The mono end capped poly(alkylene glycol) can comprise more elaborate chemical end groups, represented by the general formula (14):

$$Z''\text{—}[C(R^7)_2(C(R^7)_2)_{a'}C(R^7)_2O]_{n-1}\text{—}H \quad (14),$$

wherein Z" is a monovalent radical including the backbone carbons and oxygen of the end repeat unit, and can have 2 to 100 carbons. The following non-limiting examples illustrate mono end-derivatization of poly(ethylene glycol) (PEG). As described above, one end repeat unit of PEG can be capped with a monovalent hydrocarbon group having 1 to 20 carbons, such as the mono methyl PEG (MPEG), wherein Z" is MeOCH$_2$CH$_2$O—. The dash on the end of the MeOCH$_2$CH$_2$O— indicates the point of attachment to the polyether chain. In another example, Z" includes a thiol group, such as HSCH$_2$CH$_2$O—, or a thioether group, such as MeSCH$_2$CH$_2$O—. In another example, one end unit of PEG is an aldyhyde, wherein Z" can be OCHCH$_2$CH$_2$O—. Treating the aldehyde with a primary amine produces an imine, wherein Z" is $R^9$N=CHCH$_2$CH$_2$O—. $R^9$ is a monovalent radical selected from hydrogen, an alkyl group of 1 to 30 carbons, or an aryl group comprising 6 to 100 carbons. Continuing, the imine can be reduced to an amine, wherein Z" is $R^9$NHCH$_2$CH$_2$CH$_2$O—. In another example, one end repeat unit of PEG can be oxidized to a carboxylic acid, wherein Z" is HOOCCH$_2$O—. Using known methods the carboxylic acid can be converted to an ester, wherein Z" becomes $R^9$OOCCH$_2$O—. Alternatively, the carboxylic acid can be converted to an amide, wherein Z" becomes $R^9$NHOCCH$_2$O—. Many other derivatives are possible. In a particular embodiment, Z" is a group comprising a biologically active moiety that interacts with a specific cell type. For example, the Z" group can comprise a galactose moiety which specifically recognizes liver cells. In this instance, Z" has the structure:

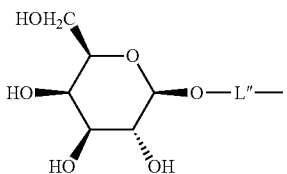

wherein L" is a divalent linking group comprising 2 to 50 carbons. The hyphen on the right side of L" indicates the attachment point to the polyether chain. Z" can comprise other biologically active moieties such as a mannose moiety.

The ring-opening polymerization can be performed with or without the use of a solvent, more particularly with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl compound concentration is about 0.1 to 5 moles per liter, and more particularly about 0.2 to 4 moles per liter. In a specific embodiment, the reaction mixture for the ring-opening polymerization contains no solvent.

The ring-opening polymerization of the first and/or second cyclic carbonyl monomer can be performed at a temperature that is about ambient temperature or higher, more specifically a temperature from 15° C. to 200° C., and more particularly 20° C. to 60° C. Reaction times vary with solvent, temperature, agitation rate, pressure, and equipment, but in general the polymerizations are complete within 1 to 100 hours.

Whether performed in solution or in bulk, the polymerizations are conducted in an inert (e.g., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The optional nitrogen base accelerator, when present, is present in an amount of 0.1 to 5.0 mol %, 0.1 to 2.5 mol %, 0.1 to 1.0 mol %, or 0.2 to 0.5 mol %, based on total moles of cyclic carbonyl compound.

The amount of initiator is calculated based on the equivalent molecular weight per nucleophilic initiating group in the initiator (e.g., hydroxy groups). The initiating groups are present in an amount of 0.001 to 10.0 mol %, 0.1 to 2.5 mol %, 0.1 to 1.0 mol %, and 0.2 to 0.5 mol %, based on total moles of cyclic carbonyl compound. For example, if the molecular weight of the initiator is 100 g/mole and the initiator has 2 hydroxy groups, the equivalent molecular weight per hydroxy group is 50 g/mole. If the polymerization calls for 5 mol % hydroxy groups per mole of monomer, the amount of initiator is 0.05×50=2.5 g per mole of monomer.

In a specific embodiment, the ring opening catalyst is present in an amount of about 0.2 to 20 mol %, the optional accelerator is present in an amount of 0.1 to 5.0 mol %, and the hydroxy groups of the initiator are present in an amount of 0.1 to 5.0 mol % based on the equivalent molecular weight per nucleophilic initiator group in the initiator.

The ring opening polymerization forms a ROP polymer comprising a living polymer chain. The living polymer chain can comprise a terminal hydroxy group, terminal thiol group, or terminal amine group, each of which can initiate further ROP chain growth, if desired. At least one repeat unit of the ROP polymer comprises a side chain pentafluorophenyl carbonate group.

The ROP polymer can comprise a linear polymer, a cyclic polymer, a graft copolymer, and other polymer topologies. The ROP polymer can be a random copolymer, an alternating copolymer, a gradient copolymer, or a block copolymer. Block copolymerization may be achieved by sequentially polymerizing different cyclic carbonyl monomers or by simultaneously copolymerizing monomers with the appropriate reactivity ratios. The ROP polymer can comprise hydrophilic repeat units, hydrophobic repeat units, and combinations thereof, thereby imparting amphiphilic properties to first ROP polymer. In an embodiment, the ROP polymer has a backbone comprising a polycarbonate homopolymer, a polycarbonate copolymer, or a polyestercarbonate copolymer.

In a preferred embodiment, the catalyst, accelerator, and reaction conditions are selected such that the growing chain end (a nucleophilic alcohol) will not react intramolecularly with a pendant pentafluorophenyl carbonate group of the same polymer chain to form a cyclic structure, or intermolecularly with a pendant pentafluorophenyl carbonate group of another polymer chain. In this way, linear polymers with controlled polydispersities can be synthesized. At high conversions when the relative concentration of monomer is low, reaction with pendant pentafluorophenyl carbonate groups can occur with subsequent broadening of the polydispersity.

If the reaction conditions permit (e.g., when a strongly activating catalyst is used), the growing chain end (e.g., a nucleophilic alcohol) can react with the pendant pentafluorophenyl carbonate side chain group of an unreacted first cyclic carbonate monomer or a pendant pentafluorophenyl carbonate side chain group of the same (i.e., an intramolecular reaction) or another polymer chain (i.e., an intermolecular reaction). Reaction with a pendant pentafluorophenyl carbonate side chain group of an unreacted first cyclic carbonate monomer will result in the formation of a macromer, which can subsequently be polymerized to make a comb or graft polymer. Intramolecular reaction can produce a cyclic structure, while intermolecular reaction can afford a branched polymer. If strongly forcing reaction conditions are used, the growing chain end can also react with the carbonyl group (e.g. ester, carbonate . . . etc.) of the polymer main chain and lead to macrocyclization or segmental exchange (by transesterification for example). Such conditions should be avoided if one wants to produce polymers with controlled molecular weights and polydispersities.

Alternatively, if a comonomer comprising additional nucleophilic groups (e.g., OX-BHMP) is used in the preparation of the first ROP polymer comprising a pentafluorophenyl carbonate side chain group, then these additional nucleophilic groups can serve as initiator groups (which initiate polymer chains), as well as nucleophilic groups that can react with the pendant pentafluorophenyl carbonate side chain groups. If the additional nucleophilic groups only serve as initiator groups, the result of the synthesis can be a first ROP polymer comprising a pentafluorophenyl carbonate side chain group with a branched, hyperbranched, comb, bottlebrush, or other such structure. If the reaction conditions permit, the additional nucleophilic groups can also react with the pendant pentafluorophenyl carbonate side chain groups of an unreacted first cyclic carbonate monomer or a pendant pentafluorophenyl carbonate side chain group of the same (i.e., an intramolecular reaction) or another polymer chain (i.e., an intermolecular reaction). Intramolecular reaction can produce a cyclic structure, while intermolecular reaction can afford a polymeric crosslinked network or gel (which might or might not have any residual pentafluorophenyl carbonate side chain groups remaining). Again, strongly forcing reaction conditions can allow these nucleophilic groups to also react with the carbonyl groups (e.g. ester, carbonate . . . etc.) of the polymer main chains, although this is generally undesirable.

The first ROP polymer can be a homopolymer, copolymer, or block copolymer. The polymer can have a number-average molecular weight of usually 1,000 to 200,000, more particularly 2,000 to 100,000, and still more particularly 5,000 to 80,000. In an embodiment, the first ROP polymer chain has a number average molecular weight $M_n$ of 10000 to 20000 g/mole. The first ROP polymer chains can also have a narrow polydispersity index (PDI), generally from 1.01 to 1.35, more particularly 1.1 to 1.30, and even more particularly 1.1 to 1.25.

Method 4. Functionalization of the First ROP Polymer.

Further disclosed is a method (Method 4) of converting the first ROP polymer into a functionalized second polymer by reaction of the pendant pentafluorophenyl carbonate side chain group of the first ROP polymer with a suitable nucleophile. The method can be performed using mild conditions, without disruption of the backbone carbonyl groups of the first ROP polymer. As a non-limiting example, the functionalization of first ROP polymer BnOH—[P(MTCPFP)] using nucleophile R"-XH is illustrated in Scheme 8.

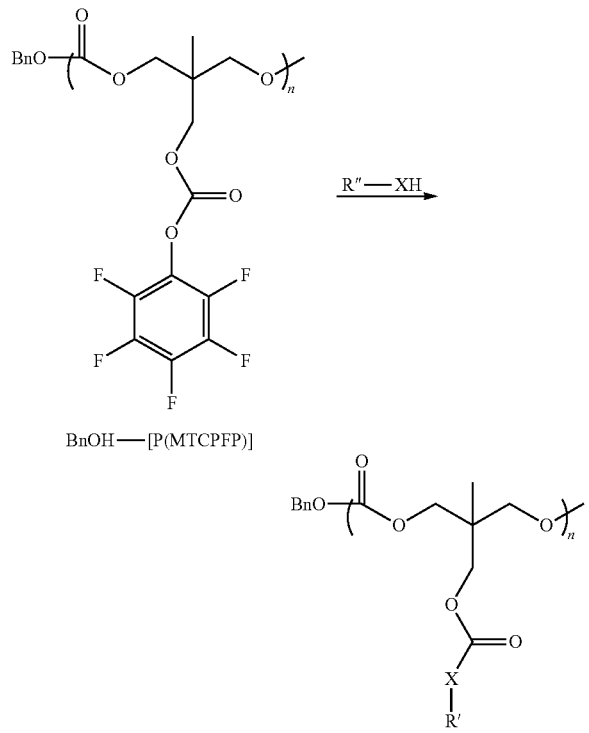

R"-XH is a nucleophile selected from the group consisting of alcohols, amines, thiols, and combinations thereof, wherein R" is without restriction with the proviso that a useful polymer is obtained. In an embodiment, R" comprises 1 to 10000 carbons. The functionalized second polymer can be prepared having essentially no remaining pentafluorophenyl carbonate groups.

The method (Method 4) comprises forming a first mixture comprising the first ROP polymer comprising a pentafluorophenyl carbonate side chain group, an optional second catalyst, a nucleophile selected from the group consisting of alcohols, amines, thiols, and combinations thereof, and an optional solvent. The first mixture is agitated and optionally heated to effect reaction of the pentafluorophenyl carbonate group with the nucleophile, thereby forming a functionalized second polymer comprising a pendant functional group selected from the group consisting of carbonates other than a pentafluorophenyl carbonate, carbamates, thiocarbonates, and combinations thereof, and pentafluorophenol byproduct.

The first ROP polymer can be treated with a variety of nucleophiles to form a functionalized second polymer. Exemplary nucleophiles include but are not limited to polymeric and non-polymeric alcohols, thiols, and amines described further above under Method 2 and Method 3. When the nucleophile is a polyether alcohol, the functionalized second polymer comprises a side chain carbonate group comprising a hydrophilic polyether chain.

The nucleophile can further comprise isotopically enriched versions of carbon, nitrogen and hydrogen, including for example $^{13}C$, $^{14}C$, $^{15}N$, deuterium, or combinations thereof. The amine can also comprise a radioactive moiety including a heavy metal radioactive isotope. Method 2 described above can also include a nucleophile comprising isotopically enriched versions of carbon, nitrogen, and hydrogen, as well as a radioactive moiety.

The nucleophile can further comprise additional reactive functional groups including hydroxy, amino, thiol, vinyl, allyl, propargyl, acetylene, azide, glycidyl, furan, furfuryl, acrylate, methacrylate, vinyl phenyl, vinyl ketone, vinyl ether, crotyl, fumarate, maleate, maleimide, butadiene, cyclopentadiene, cyclohexadiene, and derivatives thereof. These additional reactive groups may serve as sites for additional subsequent modification through Diels-Alder or Huisgen 1,3-dipolar cycloadditions, for example.

The nucleophile comprising an alcohol group, amine group, thiol group, or combination thereof can be attached to a larger structure including oligomers, polymers, biomacromolecules, particles, and functionalized surfaces. Non-limiting oligomeric and polymeric structures include linear, branched, hyperbranched, cyclic, dendrimeric, block, graft, star, and other known polymer structures. Non-limiting biomacromolecules include carbohydrates, proteins, DNA, RNA, lipids, phospholipids. Particles comprising the nucleophilic groups can have an average diameter ranging from less than 1 nanometer to hundreds of micrometers. Non-limiting functionalized surfaces include silica, alumina, and polymeric resins such as those commonly used for chromatography and functionalized polymeric beads such as those commonly used for solid-phase synthesis.

When multifunctional nucleophiles are used (e.g., diamines, triamines, diols, triols, or aminoalcohols), the functionalization reaction can result in the formation of a functionalized second polymer comprising a crosslinked network or gel. The multifunctional nucleophile can thereby serve as a crosslinking agent by reacting with pentafluorophenyl carbonate groups from different polymer chains.

Nanoparticulate nucleophiles comprising an alcohol, amine, thiol, or combination thereof, can have an average diameter of from 1 nm to 500 nm. The nanoparticles can comprise both organic and inorganic nanoparticles, including those functionalized with ligands or stabilizing polymers. Organic nanoparticles can include, but are not limited to, crosslinked polymeric nanoparticles, dendrimers, and star polymers. Inorganic nanoparticles include but are not limited to metallic nanoparticles (e.g., gold, silver, other transition metals, and Group 13 to Group 16 metals of the Periodic Table), oxide nanoparticles (e.g., alumina, silica, hafnia, zirconia, zinc oxide), nitride nanoparticles (e.g., titanium nitride, gallium nitride), sulfide nanoparticles (e.g., zinc sulfide) semiconducting nanoparticles (e.g., cadmium selenide). Functionalized surfaces include, but are not limited to, surfaces functionalized with self-assembled monolayers.

The reaction of the first ROP polymer with a nucleophile is generally conducted in a reactor under a dry inert atmosphere such as nitrogen or argon. The reaction can be performed using an inactive solvent such as benzene, toluene, xylene, dioxane, chloroform and dichloroethane, methylene chloride, tetrahydrofuran, acetonitrile, N,N-dimethyl formamide, dimethylsulfoxide, dimethyl acetamide, or mixtures thereof. The functionalization reaction temperature can be from 20° C. to 250° C. Generally, the reaction mixture is agitated at room temperature and atmospheric pressure for 0.5 to 72 hours to effect complete conversion of the pentafluorophenyl carbonate groups. Subsequently, an additional nucleophile and catalyst can be added to the second mixture to effect further functionalization of any non-reacted pentafluorophenyl carbonate groups. Alternatively, an additional nucleophile and coupling reagent can be added to the second mixture to effect functionalization of any hydroxy groups that have formed by hydrolysis of the pendant pentafluorophenyl carbonate groups.

Typically, the first mixture comprises a solvent, although this is not required. Depending on the solvent, the pentafluorophenol byproduct can in some instances precipitate directly from the reaction mixture as it is formed. Generally, however, the functionalized second polymer can be isolated by precipitation using a suitable non-solvent such as isopropanol. In this manner the functionalized second polymer can be obtained in a yield of about 50% to about 100%, more particularly about 70% to 100%, even more particularly about 80% to 100%.

The optional catalyst of the first mixture (Method 4) can be selected from typical catalysts for transesterifications, conversions of esters to amides, or conversion of esters to thioesters. These include organic catalysts and inorganic catalysts, in particular the above described catalysts, and most specifically cesium fluoride. When used in the first mixture, the catalyst can be present in an amount of 0.02 to 1.00 moles per mole of cyclic carbonyl monomer used to prepare the first ROP polymer, more particularly 0.05 to 0.50 moles per mole of the cyclic carbonyl monomer used to prepare the first ROP polymer, and even more particularly 0.15 to 0.25 moles per mole of the cyclic carbonyl monomer used to prepare the ROP polymer.

In an additional embodiment, the polymerization to form the first ROP polymer (Method 3) comprising a pendant pentafluorophenyl carbonate group, and the subsequent reaction of the first ROP polymer with a nucleophile to form a functionalized second polymer (Method 4) by displacement of the pentafluorophenoxy group of the pendant pentafluorophenyl carbonate, are conducted step-wise in a single reaction vessel, without an intermediate step to isolate the first ROP polymer bearing the side chain pentafluorophenyl carbonate group.

The above-described methods provide a controlled process for introducing a wide range of functionality and connectivity into polymers formed by ring-opening polymerizations of cyclic carbonyl compounds comprising a pendant pentafluorophenyl carbonate group. The first ROP polymer and the functionalized second polymer are particularly advantageous because they can be obtained with minimal metal contaminant when produced by an organocatalyst whose chemical formula has none of the following metals: beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table.

In preferred embodiments, the first ROP polymer and/or the functionalized second polymer contains no more than 1000 ppm (parts per million), preferably no more than 100 ppm, more preferably no more than 10 ppm, and still more preferably no more than 1 ppm, of every individual metal of the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. For example, if the limit is no more than 100 ppm, then each of the foregoing metals has a concentration not exceeding 100 ppm in the first ROP polymer, the functionalized second polymer, or both. When an individual metal concentration is below detection capability or has a concentration of zero parts, the concentration is expressed as 0 ppm. In another embodiment, every individual metal of the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration of 0 ppm to 1000 ppm, 0 ppm to 500 ppm, 0 ppm to 100 ppm, 0 ppm to 10 ppm, or even more particularly 0 ppm to 1 ppm in the first ROP polymer, the functionalized second polymer, or both. For example, if the concentration can have a value in the range of 0 ppm to 100 ppm (inclusive), then each of the foregoing metals has a concentration of 0 ppm to 100 ppm in the first ROP polymer, the functionalized second polymer, or both. In another embodiment, the first ROP polymer, the functionalized second polymer, or both comprises less than 1 ppm of every individual metal of the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. To be clear, if the limit is less than 1 ppm, then each of the foregoing metals has a concentration of less than 1 ppm in the first ROP polymer, the functionalized second polymer, or both.

The polymer products of the ROP polymerizations can be applied to conventional molding methods such as compression molding, extrusion molding, injection molding, hollow molding and vacuum molding, and can be converted to molded articles such as various parts, receptacles, materials, tools, films, sheets and fibers. A molding composition can be prepared comprising the polymer and various additives, including for example nucleating agents, pigments, dyes, heat-resisting agents, antioxidants, weather-resisting agents, lubricants, antistatic agents, stabilizers, fillers, strengthened materials, fire retardants, plasticizers, and other polymers. Generally, the molding compositions comprise 30 wt. % to 100 wt. % or more of the polymer based on total weight of the molding composition. More particularly, the molding composition comprises 50 wt. % to 100 wt. % of the polymer.

The first ROP polymer and the functionalized second polymer can be formed into free-standing or supported films by known methods. Non-limiting methods to form supported films include dip coating, spin coating, spray coating, doctor blading. Generally, such coating compositions comprise 0.01 wt. % to 90 wt. % of the polymer based on total weight of the coating composition. More particularly, the molding composition comprises 1 wt. % to 50 wt. % of the polymer based on total weight of the coating composition. The coating compositions generally also include a suitable solvent necessary to dissolve the polymer product.

The coating compositions can further include other additives selected so as to optimize desirable properties, such as optical, mechanical, and/or aging properties of the films. Non-limiting examples of additives include surfactants, ultraviolet light absorbing dyes, heat stabilizers, visible light absorbing dyes, quenchers, particulate fillers, and flame retardants. Combinations of additives can also be employed.

The second cyclic carbonyl compounds, particularly cyclic carbonate compounds can also bear polymerizeable functional groups which can be polymerized by ROP, free-radical, CRP, or other polymerization techniques. For example, monomers TMCEMA (Example 5) and TMCNSt (Example 8) bear unsaturated groups which can be polymerized via free radical or controlled radical polymerization techniques, including nitroxide-mediated radical polymerization, atom transfer radical polymerization (ATRP), and reversible addition-fragmentation polymerization (RAFT). These monomers can be polymerized through the cyclic carbonyl group, the polymerizeable functional group, or both. The cyclic carbonyl group and the polymerizeable functional group can be polymerized in any order (e.g., ROP of a cyclic carbonate and then polymerization of the functional group, vice versa, or simultaneously). Alternatively, the functional group can be polymerized (or copolymerized) to afford a polymer with pendant cyclic carbonyl groups. These cyclic carbonyl groups can then be reacted to append groups to the polymer. For example, ring-opening reactions of cyclic carbonates with primary or secondary amines are well known to produce hydroxy carbamates.

EXAMPLES

Unless indicated otherwise, parts are parts by weight, temperature is in ° C. and pressure is at or near atmospheric. Bis(pentafluorophenyl)carbonate was obtained from Central Glass Co., Ltd. (Japan). All the other starting materials were obtained (in anhydrous grade if possible) from Aldrich Chemical Co. $^1$H, $^{13}$C and $^{19}$F nuclear magnetic resonance (NMR) spectra were obtained at room temperature on a Bruker Avance 400 spectrometer.

The following Example 1 illustrates the method of making a first 6-membered cyclic carbonate compound, TMCPFP. Example 2 illustrates the method of making a first 5-membered cyclic carbonate compound, GLCPFP. Examples 3 to 8 illustrate methods of displacing the PFP carbonate of TMCPFP to form a variety of second cyclic carbonate compounds comprising different carbonate or carbamate groups. Example 9 illustrates a method of displacing the PFP carbonate of GLCPFP to form a second cyclic carbonate compound comprising a carbamate group. Example 10 illustrates the polymerization of a second cyclic carbonate monomer bearing a reactive side group. Example 11 illustrates the polymerization of a first cyclic carbonate to create a block copolymer. Example 12 illustrates the post-polymerization functionalization of the block copolymer of Example 11 to afford a polymer with functionalized carbamate side groups.

Example 1

Preparation of (5-methyl-2-oxo-1,3-dioxan-5-yl) methyl perfluorophenyl carbonate (TMCPFP)

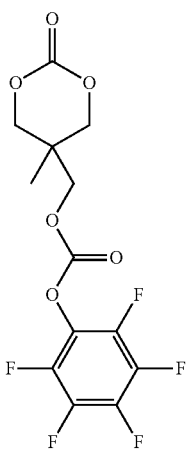

TMCPFP

To a 100 mL round bottom flask, 1,1,1-tris(hydroxymethyl)ethane (2.0 g, 16.7 mmol) was combined with bis(pentafluorophenyl)carbonate (15.1 g, 38.3 mmol, 2.3 eq.) and cesium fluoride (0.76 g, 5.0 mmol, 0.3 eq.) in anhydrous tetrahydrofuran (THF) (11.9 mL) and stirred for four hours at room temperature. Initially the reaction was heterogeneous, but after one hour the reaction formed a clear homogeneous solution. The reaction was concentrated in vacuo (100 mm Hg, 30° C.) and the residue was dissolved in methylene chloride (~50 mL). Upon standing (~10 min), the pentafluorophenol byproduct precipitated from solution and was recovered by filtration. The mother liquor was washed with aqueous sodium bicarbonate (3×50 mL) until the pH of aqueous layer was ~8 and then with brine (1×50 mL). The organic layer was separated and dried over anhydrous sodium sulfate. The solution was concentrated to give the crude product that was purified by recrystallization. The crude product was dissolved in ethyl acetate (24 mL) at 65° C. n-Hexane (35 mL) was added at the same temperature, and the resulting solution was allowed to cool to room temperature. After stirring the solution overnight, the white crystalline product TMCPFP was separated by filtration (4.0 g, 67% yield). m.p. 130-131° C. $^1$H NMR (CDCl$_3$, 400 Hz) 1.22 (s, 3H), 4.23 (d, 2H, J=11 Hz), 4.37 (s, 2H), 4.38 (d, 2H, J=11 Hz). $^{19}$F NMR (CDCl$_3$, 376 Hz) −154.3-154.3 (m, 2F), −157.8 (t, 1F, J=22 Hz), −162.6~-162.7 (m, 2F). $^{13}$C NMR (CDCl$_3$, 100 Hz) 16.8, 32.6, 70.3, 73.0, 125.4, 137.9, 140.1, 141.3, 147.4, 151.1.

Example 2

Preparation of (2-oxo-1,3-dioxolan-4-yl)methyl perfluorophenyl carbonate (GLCPFP)

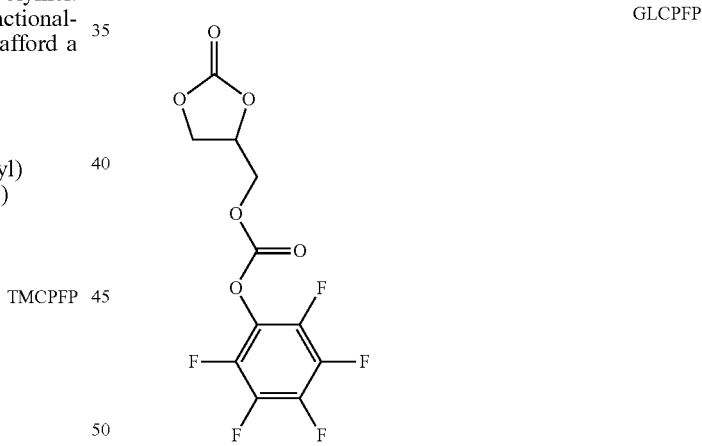

GLCPFP

Glycerin (1.0 g, 0.011 mmol) was combined with bis(pentafluorophenyl carbonate) (9.8 g, 0.025 mmol, 2.3 eq) and CsF (0.49 g, 0.033 mmol, 0.3 eq) in THF (15.6 mL) and stirred for 6 hours at room temperature. Initially the reaction was heterogeneous, but after one hour the reaction formed a clear homogeneous solution. The reaction was concentrated, and redissolved in methylene chloride. After sitting for 10 minutes, the pentafluorophenol byproduct fell out of the solution. After removal of the byproduct by filtration, the mother liquid was washed brine. The organic layer was separated and dried by NaSO$_4$. The solution was concentrated to give the crude product. The crude was dissolved with n-hexane (2 mL), and a seed crystal was added to the solution. After keeping the solution at 0° C. for one hour, the crystal was separated by filtration (2.97 g, y. 83%).

Example 3

Preparation of ethyl (5-methyl-2-oxo-1,3-dioxan-5-yl)methyl carbonate (TMCEt)

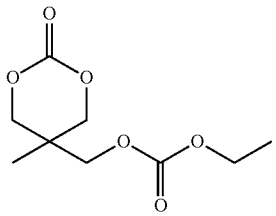
TMCEt

Under a dry nitrogen atmosphere, anhydrous ethanol (0.06 g, 1.26 mmol, 1.5 eq.) was added to the solution of TMCPFP (0.3 g, 0.84 mmol) and cesium fluoride (0.038 g, 0.25 mmol, 0.3 eq.) in THF (3 mL). The mixture was stirred for 1 day at room temperature. After the reaction, the solution was concentrated in vacuo and redissolved in methylene chloride. Upon standing (~10 min) the pentafluorophenol byproduct precipitated from solution and was removed by filtration. The crude product was purified by column chromatography (ethyl acetate/n-hexane=1/3) to give TMCEt as a white crystalline powder (0.11 g, 63% yield). m.p. 68-69° C. $^1$H NMR (CDCl$_3$, 400 Hz) 1.15 (s, 3H), 1.33 (t, 3H, J=7 Hz), 4.14 (s, 2H), 4.15 (d, 2H, J=11 Hz), 4.23 (q, 2H, J=7 Hz), 4.34 (d, 2H, J=11 Hz). $^{13}$C NMR (CDCl$_3$, 100 Hz) 14.2, 16.9, 32.3, 64.7, 67.8, 73.3, 147.7, 154.7.

Example 4

Preparation of benzyl (5-methyl-2-oxo-1,3-dioxan-5-yl)methyl carbonate (TMCBn)

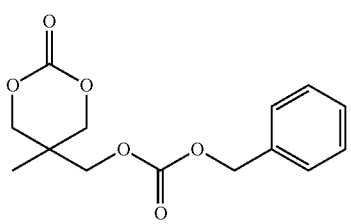
TMCBn

Under a dry nitrogen atmosphere, anhydrous benzyl alcohol (0.06 g, 0.55 mmol, 1.0 eq.) was added to the solution of TMCPFP (0.2 g, 0.55 mmol) and pyridine (0.04 g, 0.49 mmol, 0.89 eq.) in THF (2 mL). The mixture was stirred for 3 days at 55° C. After the reaction, the solution was concentrated and redissolved in methylene chloride. Upon standing (~10 min) the pentafluorophenol byproduct precipitated from solution. After removal of the byproduct by filtration, the mother liquor was washed with aqueous sodium bicarbonate (pH of aqueous layer ~8) and brine. The organic layer was separated and dried over anhydrous sodium sulfate. The solution was concentrated to give the crude product which was purified by recrystallization (toluene/n-hexane 3:1) to give TMCBn as a white crystalline powder (0.03 g, 20% yield). m.p. 72-75° C. $^1$H NMR (CDCl$_3$, 400 Hz) 1.14 (s, 3H), 4.13 (d, 2H, J=11 Hz), 4.16 (s, 2H), 4.32 (d, 2H, J=11 Hz), 5.18 (s, 2H), 7.38-7.39 (m, 5H). $^{13}$C NMR (CDCl$_3$, 100 Hz) 17.0, 32.4, 68.1, 70.3, 73.2, 128.6, 128.7, 128.9, 134.6, 147.5, 154.6.

Example 5

Preparation of 2-(((5-methyl-2-oxo-1,3-dioxan-5-yl)methoxy)carbonyloxy)ethyl methacrylate (TMCEMA)

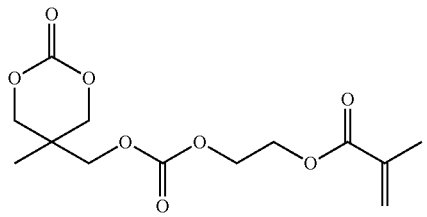
TMCEMA

Under a dry nitrogen atmosphere, 2-hydroxyethyl methacrylate (0.037 g, 0.28 mmol, 1.0 eq.) was added to the solution of TMCPFP (0.1 g, 0.28 mmol) and cesium fluoride (0.013 g, 0.084 mmol, 0.3 eq.) in THF (1 mL). The mixture was stirred for 3 days at room temperature. After the reaction, the solution was concentrated and redissolved in methylene chloride. Upon standing (~10 min) the pentafluorophenol byproduct precipitated from solution and was removed by filtration. The solvent was removed in vacuo to afford a crude product that was further purified by column chromatography (ethyl acetate/n-hexane=1/3) to give TMCEMA as a colorless oil (0.03 g, 35% yield). $^1$H NMR (CDCl$_3$, 400 Hz) 1.16 (s, 3H), 1.96 (s, 3H), 4.16 (d, 2H, J=11 Hz), 4.17 (s, 2H), 4.34 (d, 2H, J=11 Hz), 3.39-4.43 (m, 2H), 5.63 (bs, 1H), 6.15 (s, 1H). $^{13}$C NMR (CDCl$_3$, 100 Hz) 17.0, 18.3, 32.4, 62.0, 66.2, 68.2, 73.2, 126.4, 135.7, 147.5, 154.6, 167.1.

Example 6

Preparation of isopropyl (5-methyl-2-oxo-1,3-dioxan-5-yl)methyl carbonate (TMCiPR)

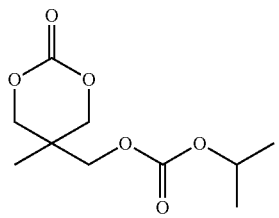
TMCiPr

Under a dry nitrogen atmosphere, anhydrous 2-propanol (0.025 g, 0.42 mmol, 1.5 eq.) was added to the solution of TMCPFP (0.1 g, 0.28 mmol) and cesium fluoride (0.013 g, 0.084 mmol, 0.3 eq.) in THF (1 mL). The mixture was stirred for 1 day at 55° C. After the reaction, the solution was concentrated and redissolved in methylene chloride. Upon standing (~10 min) the pentafluorophenol byproduct precipitated from solution and was removed by filtration. The solvent was removed in vacuo to afford a crude product that was further purified by column chromatography (ethyl acetate/n-hexane=1/3) to give TMCiPR as a white crystalline powder (0.03 g, 46% yield). m.p. 64-65° C. $^1$H NMR (CDCl$_3$, 400 Hz) 1.18 (s, 3H), 1.34 (d, 6H, J=6 Hz), 4.14 (s, 2H), 4.17 (d, 2H, J=11

Hz), 4.36 (d, 2H, J=11 Hz), 4.92 (sep, 1H, J=6 Hz). $^{13}$C NMR (CDCl$_3$, 100 Hz) 17.0, 21.7, 32.4, 67.6, 72.9, 73.3, 147.7, 154.2.

Example 7

Preparation of (5-methyl-2-oxo-1,3-dioxan-5-yl) methyl benzylcarbamate (TMCNBn)

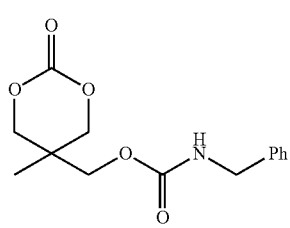

TMCNBn

Under a dry nitrogen atmosphere, anhydrous benzyl amine (0.039 g, 0.37 mmol, 1.32 eq.) was added to the solution of TMCPFP (0.1 g, 0.28 mmol) and cesium fluoride (0.013 g, 0.084 mmol, 0.3 eq.) in THF (1 mL). The mixture was stirred for 1 day at room temperature. After the reaction, the solution was concentrated and redissolved in methylene chloride. Upon standing (~10 min) the pentafluorophenol byproduct fell out of solution and was removed by filtration. The solvent was removed in vacuo to afford a crude product that was further purified by column chromatography (ethyl acetate/n-hexane=1/1) to give TMCNBn as a colorless oil (0.044 g, 56% yield). $^1$H NMR (CDCl$_3$, 400 Hz) 1.11 (s, 3H), 4.14 (d, 2H, J=11 Hz), 4.15 (s, 2H), 4.32 (d, 2H, J=11 Hz), 4.38 (d, 2H, J=6 Hz), 6.23 (bs, 1H), 7.28-7.36 (m, 5H). $^{13}$C NMR (CDCl$_3$, 100 Hz) 17.1, 32.4, 45.2, 66.1, 73.9, 127.6, 127.7, 128.7, 138.0, 148.0, 155.7.

Example 8

Preparation of (5-methyl-2-oxo-1,3-dioxan-5-yl) methyl 4-vinylphenylcarbamate (TMCNSt)

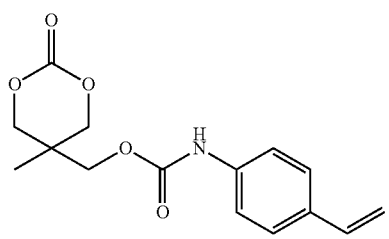

TMCNSt

Under a dry nitrogen atmosphere, 4-vinylaniline (0.87 g, 7.3 mmol, 1.3 eq.) was added to the solution of TMCPFP (2.0 g, 5.6 mmol) and cesium fluoride (0.26 g, 1.7 mmol, 0.3 eq.) in THF (11.2 mL). The mixture was stirred for 2 days at room temperature. The solution was concentrated and the residue was redissolved in methylene chloride. Upon standing (~10 min) the pentafluorophenol byproduct precipitated from solution. After removal of the byproduct by filtration, the mother liquid was washed with aqueous sodium bicarbonate (pH of aqueous layer; ~8) and brine. The organic layer was separated and dried over anhydrous sodium sulfate. The solution was concentrated to give the crude product which was purified by recrystallization from toluene (40 mL) to give TMCNSt as a crystalline powder (1.3 g, 81% yield). m.p. 120-121° C. $^1$H NMR (CDCl$_3$, 400 Hz) 1.14 (s, 3H), 4.19 (d, 2H, J=11 Hz), 4.21 (s, 2H), 4.38 (s, 2H, J=11 Hz), 5.20 (d, 1H, J=11 Hz), 5.68 (d, 1H, J=18 Hz), 6.67 (dd, 1H, J=18, 11 Hz), 6.98 (bs, 1H), 7.36 (s, 4H). $^{13}$C NMR (CDCl$_3$, 100 Hz) 17.0, 32.4, 65.8, 73.8, 112.9, 118.7, 126.9, 133.2, 136.0, 137.0, 148.3, 152.7.

Example 9

Preparation of (2-oxo-1,3-dioxolan-4-yl)methyl benzylcarbamate (GLCNBn)

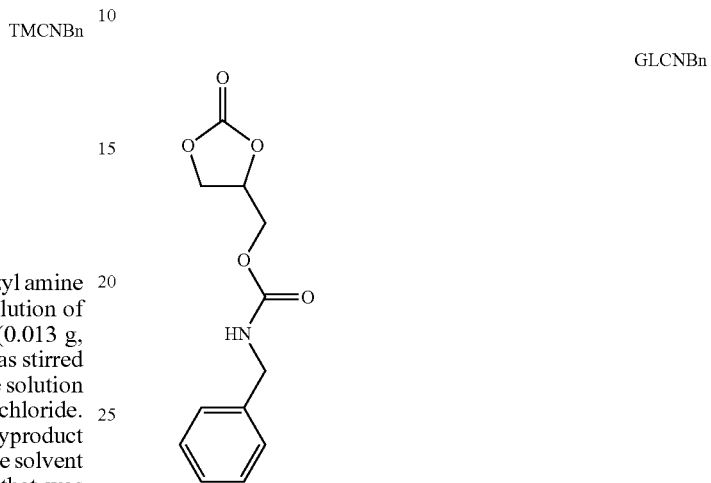

GLCNBn 5-membered cyclic carbonate (0.2 g, 0.61 mmol) and benzyl amine (0.098 g, 0.91 mmol, 1.5 eq) and CsF (0.028 g, 0.18 mmol, 0.3 eq) were combined in THF (1 mL) and stirred at room temperature. After 18 hours, the reaction mixture was concentrated, and redissolved in methylene chloride. After sitting for 10 minutes, the pentafluorophenol byproduct fell out of the solution. After removal of the byproduct by filtration, the mother liquid was washed with aqueous ammonium chloride. The organic layer was separated and dried by NaSO$_4$. The solution was concentrated to give the crude product. The crude was recrystallized from methylene chloride (2 mL) and n-hexane (1.5 mL). The crystal was separated by filtration (0.080 g, y. 56%).

Example 10

Preparation of BnOH—[P(TMCNSt)] by Ring Opening Polymerization of TMCNSt

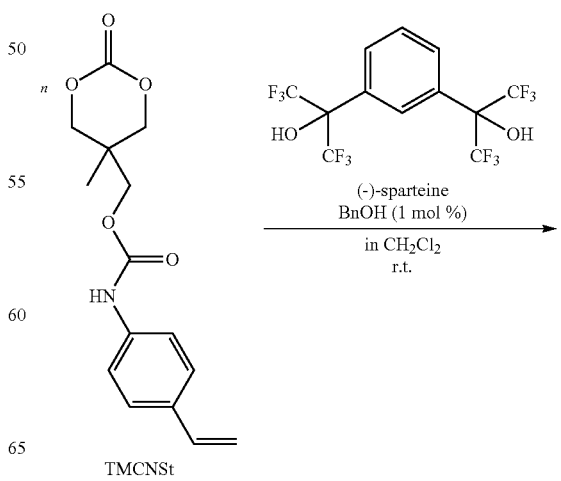

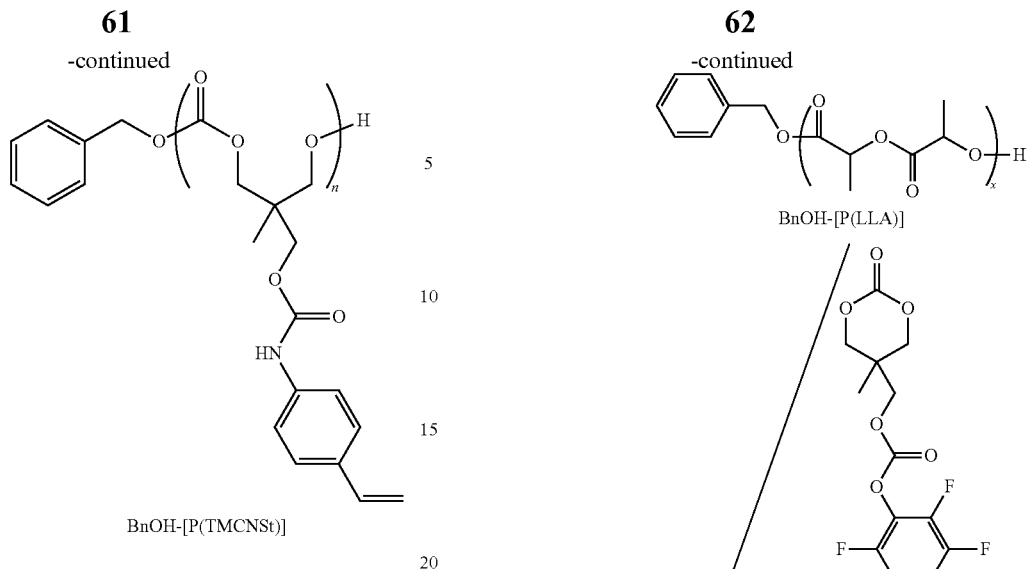

BnOH-[P(TMCNSt)]

Under a dry atmosphere, TMCNSt (296 mg, 0.924 mmol), 1,3-bis(1,1,1,3,3,3-hexafluoro-2-hydroxy-prop-2-yl)benzene (19 mg, 0.046 mmol, 0.05 eq), (−)-sparteine (11 microliters, 0.046 mmol, 0.05 eq.), benzyl alcohol (0.97 microliter, 0.009 mmol, 0.01 eq.), and methylene chloride (2 mL, 0.5M) were combined in a flask and stirred for 3 days at room temperature. $^1$H NMR revealed the conversion to be 90%. The polymer BnOH—[P(TMCNSt)] was precipitated in methanol. $M_n$=4269 g/mol. $M_w$=6935 g/mol. PDI=1.62.

Example 11

Preparation of BnOH—[P(LLA-b-TMCPFP)] Block Copolymer

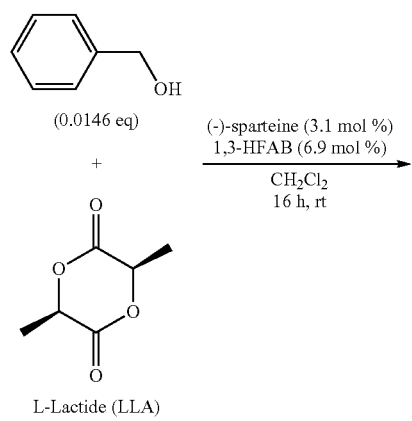

L-lactide (1.92 g, 13.3 mmol), 1,3-HFAB (376 mg, 0.916 mmol, 0.069 eq), (−)-sparteine (98 mg, 0.417 mmol, 0.031 eq), and benzyl alcohol (21 mg, 0.194 mmol, 0.0146 eq) were combined in dichloromethane (15 mL) and stirred at room temperature. After 16 hours, TMCPFP (1.19 g, 3.34 mol) was added and the solution was allowed to stir at room temperature for an additional 24 hours. The crude block copolymer was isolated via precipitation from 2-propanol. The crude product was dissolved with dichloromethane (8 mL), and the solution was added dropwise to n-hexane (15 mL) to remove unreacted TMCPFP. The mother liquor was evaporated to give the block copolymer BnOH—[P(LLA-b-TMCPFP)]. Approximately, 99% of the pentafluorophenyl carbonate groups were retained after isolation. Incorporation ratio (LLA/TMCPFP): 95.8/4.2. $M_n$=10400 g/mol. $M_w$=10,800 g/mol. PDI=1.04.

Example 12

Functionalization of BnOH—[P(LLA-b-TMCPFP)]

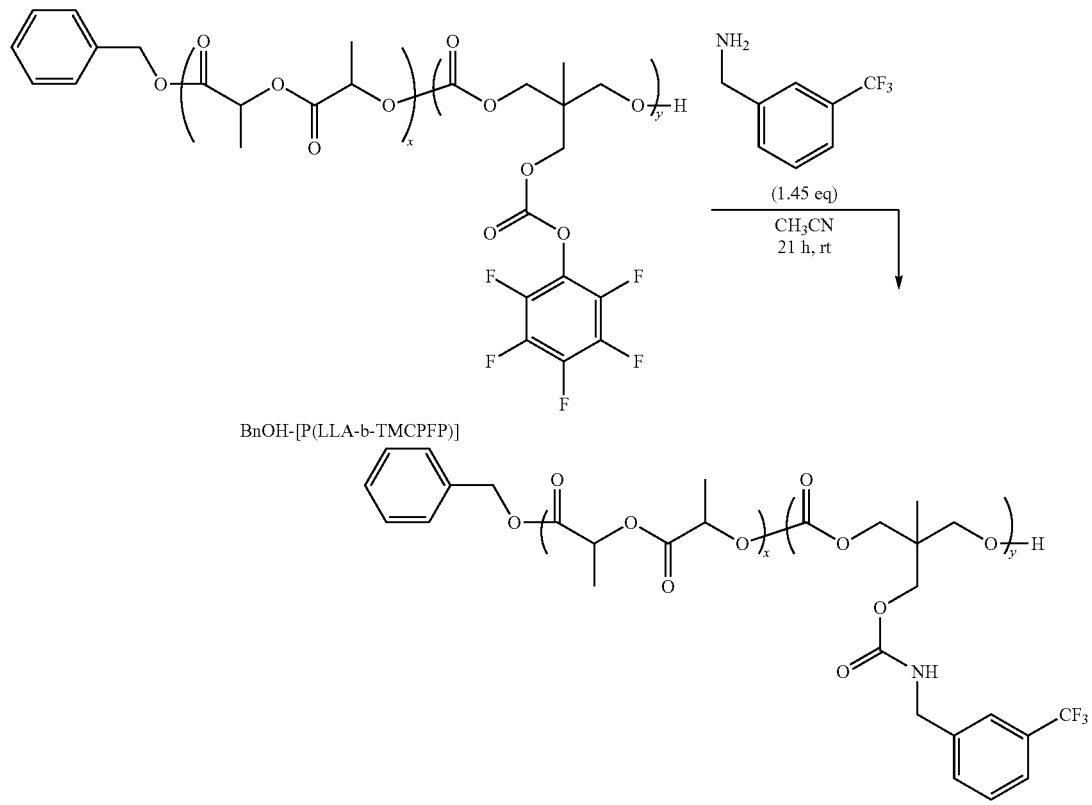

BnOH—[P(LLA-b-TMCPFP)] (0.25, 0.069 mmol (as —$C_6F_6$ carbonate)) and 3-(trifluoromethyl)benzyl amine (0.018 g, 0.10 mmol, 1.45 eq.) were dissolved in acetonitrile (0.28 g). The mixture was stirred for 21 hours at room temperature. After the reaction, the functionalized second polymer comprising a side chain carbamate group was precipitated from n-hexane. Percent substitution: 87%. Residual pentafluorophenyl carbonate: 0%. $M_n$=10,400 g/mol. $M_w$=11,000 g/mol. PDI=1.05.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two limits, (e.g., a component can have a concentration of X ppm to Y ppm, where X and Y are numbers), unless otherwise stated the value can be any number within the range, or a stated limit (i.e., X or Y) of the range.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

The invention claimed is:
1. A biodegradable polymer, comprising:
    a chain fragment; and
    a first polymer chain; wherein i) the chain fragment comprises a first backbone heteroatom, the first backbone heteroatom linked to a first end unit of the first polymer chain, the first backbone heteroatom selected from the group consisting of oxygen, nitrogen, and sulfur, ii) the first polymer chain comprises a second end unit comprising a nucleophilic group selected from the group consisting of hydroxy group, primary amine groups, secondary amine groups, and thiol group, and iii) the first polymer chain comprises a first repeat unit, the first repeat unit comprising a) a backbone functional group selected from the group consisting of carbonate, ureas, carbamates, thiocarbamates, thiocarbonate, and dithiocarbonate, and b) a tetrahedral backbone carbon, the tetrahedral backbone carbon being linked to a first side chain comprising a pentafluorophenyl carbonate group.

2. The biodegradable polymer of claim 1, wherein the first repeat unit comprises a carbonate backbone functional group.

3. The biodegradable polymer of claim 1, wherein the backbone functional group of the first repeat unit is a carbamate.

4. The biodegradable polymer of claim 1, wherein the first backbone heteroatom is oxygen.

5. The biodegradable polymer of claim 1, wherein the first backbone heteroatom is nitrogen.

6. The biodegradable polymer of claim 1, wherein the nucleophilic group of the second end unit is a hydroxy group.

7. The biodegradable polymer of claim 1, wherein the nucleophilic group of the second end unit is a primary amine or a secondary amine.

8. The biodegradable polymer of claim 1, wherein the tetrahedral backbone carbon of the first repeat unit is linked to a second side chain comprising 1 to 30 carbons.

9. The biodegradable polymer of claim 1, wherein the biodegradable polymer contains no metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table having a concentration in the biodegradable polymer of greater than 100 ppm.

10. The biodegradable polymer of claim 1, wherein the polymer undergoes 60% biodegradation within 180 days in accordance with ASTM D6400.

11. The biodegradable polymer of claim 1, wherein the first polymer is a copolymer comprising a second repeat unit, the second repeat unit comprising a backbone functional group selected from the group consisting of ester, carbonate, ureas, carbamates, thiocarbamates, thiocarbonate, and dithiocarbonate.

12. The biodegradable polymer of claim 11, wherein the backbone functional group of the second repeat unit is an ester.

13. The biodegradable polymer of claim 11, wherein the backbone functional group of the second repeat unit is a carbonate.

14. The biodegradable polymer of claim 11, wherein the second repeat unit is

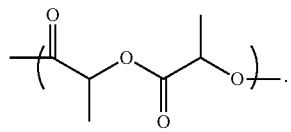

15. The biodegradable polymer of claim 14, wherein the second repeat unit is the D stereoisomer.

16. The biodegradable polymer of claim 14, wherein the second repeat unit is the L stereoisomer.

17. The biodegradable polymer of claim 1, wherein the first repeat unit has a structure

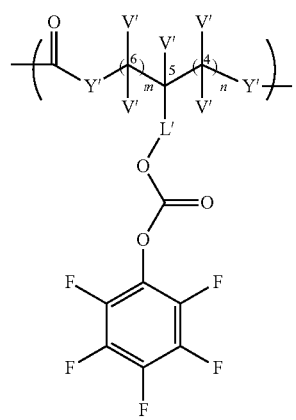

wherein
m and n are each independently 0 or an integer from 1 to 11, wherein m and n cannot together be 0, and m+n is an integer less than or equal to 11, each Y' is a divalent radical independently selected from the group consisting of —O—, —S—, —N(H)— and —N(V")—, wherein each V" is a monovalent radical independently selected from the group consisting of alkyl groups comprising 1 to 30 carbons, aryl groups comprising 1 to 30 carbons, and the members of the foregoing alkyl and aryl groups substituted with a pentafluorophenyl carbonate group (—OCO$_2$C$_6$F$_5$), each V' is a monovalent radical independently selected from the group consisting of hydrogen, halides, pentafluorophenyl carbonate group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the members of the foregoing alkyl, alkene, alkyne, aryl, ester, amide, thioester, urea, carbamate, ether, and alkoxy groups substituted with a pentafluorophenyl carbonate group, and L' is a single bond or a divalent linking group selected from the group consisting of alkylene groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

18. The biodegradable polymer of claim 17, wherein each Y' is —O—, m=1, and n=1.

19. The biodegradable polymer of claim 17, wherein V' at carbon 5 is methyl, ethyl, or propyl, and all other V' are hydrogen.

20. The biodegradable polymer of claim 17, wherein L' is methylene.

* * * * *